US011400151B2

(12) United States Patent
Haffer

(10) Patent No.: US 11,400,151 B2
(45) Date of Patent: Aug. 2, 2022

(54) METHODS FOR IMPROVING IMMUNOLOGICAL RESPONSE IN VACCINATED ANIMALS

(71) Applicant: Braasch Biotech LLC, Garretson, SD (US)

(72) Inventor: Keith N. Haffer, Garretson, SD (US)

(73) Assignee: Braasch Biotech LLC, Garretson, SD (US)

( * ) Notice: Subject to any disclaimer, the term of this patent is extended or adjusted under 35 U.S.C. 154(b) by 0 days.

(21) Appl. No.: 16/552,442

(22) Filed: Aug. 27, 2019

(65) Prior Publication Data

US 2019/0374634 A1   Dec. 12, 2019

Related U.S. Application Data

(62) Division of application No. 14/831,602, filed on Aug. 20, 2015, now Pat. No. 10,441,652.

(60) Provisional application No. 62/039,977, filed on Aug. 21, 2014.

(51) Int. Cl.
| | | |
|---|---|---|
| *A61K 39/395* | (2006.01) | |
| *A61K 39/385* | (2006.01) | |
| *C12N 9/10* | (2006.01) | |
| *C07K 14/655* | (2006.01) | |
| *A61K 39/00* | (2006.01) | |

(52) U.S. Cl.
CPC ........ *A61K 39/385* (2013.01); *A61K 39/0005* (2013.01); *C07K 14/655* (2013.01); *C12N 9/1033* (2013.01); *A61K 2039/552* (2013.01); *A61K 2039/6031* (2013.01); *A61K 2039/627* (2013.01); *C07K 2319/00* (2013.01); *C07K 2319/40* (2013.01)

(58) Field of Classification Search
None
See application file for complete search history.

(56) References Cited

U.S. PATENT DOCUMENTS

| | | | |
|---|---|---|---|
| 6,025,368 | A | 2/2000 | Mascarenhas et al. |
| 6,316,004 | B1 | 11/2001 | Lunin et al. |
| 7,722,881 | B2 | 5/2010 | Mendelsohn et al. |
| 7,943,143 | B2 | 5/2011 | Mendelsohn et al. |
| 8,121,797 | B2 | 2/2012 | Heckerman et al. |
| 8,367,073 | B2 | 2/2013 | Mendelsohn et al. |
| 8,425,914 | B2 | 4/2013 | Haffer et al. |
| 10,441,652 | B2 * | 10/2019 | Haffer .................. A61K 39/385 |
| 2007/0048860 | A1 | 3/2007 | Schlom et al. |
| 2007/0249532 | A9 | 10/2007 | Guyon et al. |
| 2008/0081068 | A1 | 4/2008 | Oberegger et al. |
| 2008/0311159 | A1 | 12/2008 | Klein et al. |
| 2013/0149332 | A1 | 6/2013 | Haffer et al. |

FOREIGN PATENT DOCUMENTS

| | | |
|---|---|---|
| EP | 0645454 A2 | 3/1995 |
| KR | 10-1990-0700505 A | 8/1990 |
| WO | 2005066344 A2 | 7/2005 |
| WO | 2009157926 A1 | 12/2009 |

OTHER PUBLICATIONS

Alahari et al., "The N-Terminal Domain of OmpATb Is Required for Membrane Translocation and Pore-Forming Activity in Mycobacteria"; J Bacteriology ; 189(17): 6351-6358 (Sep. 2007).
Betts et al., "Amino Acid Properties and Consequences of Substitutions"; Bioinformatics for Geneticists; 14:289-316 (2003).
Comvax® [Haemophilus b Conjugate (Meningococcal Protein Conjugate) and Hepatitis B (Recombinant) (Vaccine) Merck & Co., Inc. Information sheet Issued Dec. 2010. 14 pages (2001).
Danoff et al., "Intracellular degradation of prohormone-chloramphenicol-acetyl-transferase chimeras in a pre-lysosomal compartment"; Eur J Biochem; 218(3):1063-1070 (Dec. 15, 1993).
Drackley, "Physiological adaptations in transition dairy cows"; p. 74-87 in Proc. Minnesota Dairy Herd Health Conf., St Paul, MN. University of Minnesota, St. Paul). (2004).
Drozdowski et al., "Intestinal mucosal adaptation"; World of Gastroenterol; 12(29):4614-4627 (2006).
Etz et al., "Identification of in vivo expressed vaccine candidate antigens from *Staphylococcus aureus*"; PNAS; 99 (10):6573-6578 (May 14, 2002).
Fortier et al., "Insulin-like growth factor enhances cell-based repair of articular cartilage"; J Bone and Joint Surgery; 84-B(2):276-288 (2002).
Frost et al., "Neutralizing antibody responses drive the evolution of human immunodeficiency virus type 1 envelope during recent HIV infection"; PNAS 102(51):18514-18519 (2005).
Gonzalez-Cadavid et al., "Organization of the human myostatin gene and expression in healthy men and HIV-infected men with muscle wasting"; PNAS USA 95:14938-14943 (Dec. 1998).
Haffer, "Effects of novel vaccines on weight loss in diet-induced-obese (DIO) mice"; J Animal Sci and Biotecch; 3:21 (2012).
Hoof et al., "NetMHCpan, a method for MHC class I binding prediction beyond humans"; Immunogenetics; 61 (1):1-13 (Jan. 2009).
International Search Report from International Patent Application PCT/US2008/068195 dated Mar. 18, 2009.
International Search Report from International Patent Application PCT/US2009/048429 dated Sep. 2, 2009.
Jaffe et al., "Endogenous growth hormone (GH)-releasing hormone is required for GH responses to pharmacological stimuli"; J Clinical Investigation; 97(4):934-940 (1996).

(Continued)

*Primary Examiner* — Yunsoo Kim
(74) *Attorney, Agent, or Firm* — Merchant and Gould, P.C.

(57) ABSTRACT

A method is provided for increasing an immunological response to a target antigen in an animal by administering an immunogenic amount of a vaccine comprising a polypeptide conjugate comprising the target antigen conjugated to a carrier polypeptide by means of a linker polypeptide which is rich in predicted linear B-cell epitopes.

19 Claims, 11 Drawing Sheets

Specification includes a Sequence Listing.

(56) References Cited

OTHER PUBLICATIONS

Kim et al., "Derivation of an amino acid similarity matrix for peptide: MHC binding and its application as a Bayesian prior"; BMC Bioinformatics; 10:394 (Nov. 30, 2009).
Kolaskar et al., "A semi-empirical method for prediction of antigenic determinants on protein antigens"; FEBS 09210; 276(1, 2):172-174 (Dec. 1990).
Larsen et al, "Improved method for predicting linear B-cell epitopes"; Immunome Research; 2:2 pp. 1-7 (Apr. 24, 2006).
Lewendon et al., "The pKa of the catalytic histidine residue of chloramphenicol acetyltransferase"; Biochem J., 290 (Pt1):15-19 (Feb. 15, 1993).
Lewendon et al., "Replacement of Catalytic Histidine-195 of Chloramphenicol Acetyltransferase: Evidence for a General Base Role for Glutamate"; Biochemistry; 33(7):1944-1950 (1994).
Liang et al., "Construction and evaluation of the eukaryotic expression plasmid encoding two copies of somatostatin genes fused with hepatitis B surface antigen gene S."; Vaccine; 26(23):2935-2941 (2008) Epub Apr. 8, 2008.
Lin et al. "Evolution of neuroendocrine peptide systems: Gonadotropin-releasing hormone and somatostatin"; Comp. Biochem. Physiol. Part C.; 119(3):375-388. (1998).
Liu et al., "A vaccine carrier derived from Neisseria meningitides with mitogenic activity for lymphocytes"; PNAS USA; 89:4633-4637 (May 1992).
Liu et al. "Insulin-like growth factor I is essential for postnatal growth in response to growth hormone"; Endocrinology; 140(11):5178-5184 (1999).
Ma, "Calcitonin Gene-Related Peptide (CGRP)"; Nature and Science 2(3):41-47 (Oct. 1, 2004).
Mapp et al., "A role for the sensory neuropeptide calcitonin gene-related peptide in endothelial cell proliferation in vivo"; British J of Pharmacology; 166:1261-1271 (2012).
Minvielle et al., "A Novel Calcitonin Carboxyl-terminal Peptide Produced in Medullary Thyroid Carcinoma by Alternative RNA Processing of the Calcitonin/Calcitonin Gene-related Peptide Gene"; J bio Chem; 266 (36):24627-24631 (Dec. 25, 1991).
Moisa et al., "Synthetic Peptide Vacines, Insight and Control of Infectious Disease in Global Scenario"; Dr. Roy Priti (Ed.), ISBN: 978-953-51-0319-6; InTech; 11:201-229. Available from: http://www.intechopen.com/books/insight-and-control-of-infectious-disease-in-global-scenario/synthetic-peptide-vaccines (2012).
Muderhwa et al., "Oil-in-water liposomal emulsions: characterization and potential use in vaccine delivery"; J Pharm Sci; 88(12):1332-1339 (Dec. 1999).
Neilsen et al., "Reliable prediction of T-cell epitopes using neural networks with novel sequence representations" Protein Sci; 12(5):1007-1017 (May 2003).
Oyarzun et al., "PREDIVAC: CD4+ T-cell epitope prediction for vaccine design that covers 95% of HLA class II DR protein diversity"; BMC Bioinformatics; 14:52-63 (2013).
Pellequer et al., "Predicting the location of continuous epitopes in proteins from their primary structure"; Methods Enzymol.; 203:176-201 (1991).
Peters et al., "Generating quantitative models describing the sequence specificity of biological processes with the stabilized matrix method"; BMC Bioinformatics; 31; 6:132 pp. 1-9 (May 31, 2005).
Pinto et al., Induction of CD8+ T cells to an HIV-1 antigen through a prime boost regimen with heterologous E1-deleted adenoviral vaccine carriers; J. Immunol. 171(12):6774-6779 (Dec. 15, 2003).
Ponomarenko et al., "Antibody-protein interactions: benchmark datasets and prediction tools evaluation"; BMC Stuctual Ciology; 7:64 (2007).
Ponomarenko et al., "B-Cell Epitope Prediction"; Structural Bioinformatics, Second Edition; ed Gu et al; 35:849-879 (2009).
Reichlin, ed., Somatostatin, Basic and Clinical Status. Plenum Press, New York, pp. 3-50, 121-136, 146-156, 169-182, 221-228, 267-274 (1987).
Schuler et al., "SYFPEITHI: Database for Searching and T-cell epitope prediction"; Methods Mol Biol.; 409:75-93 (Jun. 21, 2007).
Schutze et al., "Carrier-induced epitopic suppression, a major issue for future synthetic vaccines" J. Immunol.; 135 (4):2319-2322 (Oct. 1, 1985).
Shiratsuchi et al., "Replacing adenoviral vector HVR1 with a malaria B cell epitope improves immunogenicity and circumvents preexisting immunity to adenovirus in mice"; The Journal of clinical Investigation; 120(10):3688-3701 (Oct. 2010). (www.jci.org/articles/view/39812 downloaded on Oct. 30, 2013).
Spencer, "Hormonal Systems Regulating Growth. A Review"; Livestock Production Science; 12:31-46 (1985).
Vickers et al., "Adult growth hormone treatment reduces hypertension and obesity induced by an adverse prenatal environment"; J Endocrinology; 175:615-623 (2002).
Volokhina et al., "The Beta-Barrel Outer Membrane Protein Assembly Complex of Neisseria meningitides"; J Bacteriol, 191(22):7074-7085 (Nov. 2009).
White et al., "Characterization of Chloramphenicol and Florfenicol Resistance in *Escherichia coli* Associated with Bovine Diarrhea"; J. Clin. Microbio 38(12):4593-4598 (2000).
Wu et al., "Identification of B-Cell Epitope of Dengue Virus Type 1 and Its Application in Diagnosis of Patients"; Journal of Clinical Microbiology; 39(3):977-982 (Mar. 2001).
Invitation to Pay Additional Fees with Partial International Search Report from corresponding International Patent Application No. PCT/US2015/046105 dated Feb. 8, 2016.
International Search Report and Written Opinion for Application No. PCT/US2015/046105 dated Apr. 20, 2016.

* cited by examiner

METHODS FOR IMPROVING IMMUNOLOGICAL RESPONSE IN VACCINATED ANIMALS

CROSS-REFERENCES TO RELATED APPLICATIONS

This application is a divisional of U.S. patent application Ser. No. 14/831,602, filed Aug. 20, 2015, issued as U.S. Pat. No. 10,441,652 on Oct. 15, 2019, which claims priority to U.S. Provisional Application No. 62/039,977, filed Aug. 21, 2014, entitled "Methods for Improving Immunological Response in Vaccinated Animals", each of which is incorporated herein by reference in its entirety.

TECHNICAL FIELD

A method is provided for increasing an immunological response to a target antigen in an animal by administering an immunogenic amount of a vaccine comprising a polypeptide conjugate comprising the target antigen conjugated to a carrier polypeptide by means of a linker polypeptide which is rich in predicted linear B-cell epitopes.

BACKGROUND OF THE INVENTION

Conjugated vaccines rely on antigen attachment to a carrier protein or vector, allowing an otherwise non-immunogenic antigen to take on the immunogenicity of the carrier. Conjugated vaccines employing the widely-used tetanus toxoid carrier have been shown to have reduced efficacy in individuals previously exposed to tetanus toxoid, as pre-existing immunity against the carrier neutralizes the conjugated vaccine. Schutze et al., Carrier-induced epitopic suppression, a major issue for future synthetic vaccines. J. Immunol. 1985; 135(4):2319-22. Other common carriers, such as adenovirus, are also likely to be neutralized by pre-existing immunity, especially upon repeated vaccinations or booster injections. Pinto et al., Induction of CD8+ T cells to an HIV-1 antigen through a prime boost regimen with heterologous E1-deleted adenoviral vaccine carriers. J. Immunol. 2003p; 171(12):6774-9.

Methods are provided herein for improving a specific immune response in a subject to a target antigen having low predicted linear B-cell epitope scoring, the method comprising administering to the subject a polypeptide conjugate comprising the target antigen covalently attached to a carrier polypeptide by means of an intervening linker polypeptide, wherein the linker polypeptide and/or the carrier polypeptide exhibit higher predicted linear B-cell epitope scoring than the target antigen, and wherein the carrier polypeptide does not stimulate a substantial T-cell response.

SUMMARY OF THE INVENTION

Embodiments of the present invention provide novel methods for improving immunological response to a target antigen in a polypeptide conjugate or fusion protein.

In some embodiments, a method is provided for stimulating an improved immunological response to a target antigen in an animal, the method comprising administering an immunogenic amount of a vaccine to an animal, the vaccine comprising a polypeptide conjugate comprising (a) a carrier polypeptide comprising an inactivated chloramphenicol acetyl transferase (CAT) enzyme; (b) a linker polypeptide, and (c) a target antigen, wherein the carrier polypeptide does not stimulate a substantial T cell response.

In some embodiments, the target antigen exhibits low % predicted linear B-cell epitopes.

In some embodiments, the target antigen exhibits low % predicted linear B-cell epitopes selected from <10%, <7%, <5%, <4%, <3%, <2%, <1%, <0.1% or 0% predicted linear B-cell epitopes, wherein the % predicted linear B-cell epitopes for the target antigen is determined by
(1) generating a BepiPred 1.0 predicted Linear B-cell epitope score for each amino acid in the amino acid sequence of the target antigen;
(2) counting the amino acids for which the BepiPred 1.0 predicted Linear B-cell epitope score is above a threshold value;
(3) dividing the number of amino acids above the threshold value by the number of amino acids in the target antigen to get a fraction; and
(4) multiplying the fraction by 100 to obtain the % predicted linear B-cell epitopes for the target antigen.

In some embodiments, the linker polypeptide exhibits high % predicted linear B-cell epitopes. In some embodiments, the linker polypeptide exhibits high % predicted linear B-cell epitopes selected from >50%, >60%, >70% or >80% predicted linear B-cell epitopes, wherein the % predicted linear B-cell epitopes in the linker polypeptide is determined by
(1) generating a BepiPred 1.0 predicted Linear B-cell epitope score for each amino acid in the amino acid sequence of the linker polypeptide;
(2) counting the amino acids in the linker polypeptide for which the BepiPred 1.0 predicted Linear B-cell epitope score is above a threshold value;
(3) dividing the number of amino acids above the threshold value by the total number of amino acids in the linker polypeptide to get a fraction; and
(4) multiplying the fraction by 100 to get the % predicted Linear B-cell Epitopes for the linker polypeptide.

In some embodiments, a polypeptide conjugate is provided comprising a carrier polypeptide comprising an amino acid sequence selected from SEQ ID NO: 3, 7, 8, 26, 27, 28, or 29.

In some embodiments, a polypeptide conjugate is provided comprising a linker polypeptide that comprises an amino acid sequence selected from SEQ ID NO: 10, 11, 16, 17, 18, 19, 20, 21, 22, 23, 24, 25, 53, 54, 55, 56 or 57.

In some embodiments, methods are provided for stimulating an improved immunological response to a target antigen in an animal, wherein the improved immunological response comprises one or more of (1) a statistically significant increase in serum anti-target antigen IgG or serum anti-carrier IgG from the animal observed after the first or subsequent administration of the vaccine comprising the polypeptide conjugate, compared to control immunized with target antigen and/or carrier without the linker polypeptide, (2) a statistically significant increase or decrease in a specific effect in the animal following administration of the vaccine comprising the polypeptide conjugate compared to a control, or (3) a statistically significant faster statistically significant immunological response or specific effect in the animal following administration of the vaccine comprising the polypeptide conjugate compared to a control.

In some embodiments, the improved immunological response in the animal comprises a statistically significant faster immunological response or specific effect compared to a control, wherein the response or effect occurs within six days, five days, four days, three days, two days, or within one day following the first or subsequent administrations to the animal of the vaccine comprising the polypeptide conjugate.

In some embodiments, the specific effect is selected from increased milk production, increased body weight, increased lean body weight, decreased percent body-fat, or decreased body weight in the animal compared to a control without immunization.

In some embodiments, the immunogenicity of said target antigen in the polypeptide conjugate is increased as compared to the target antigen in the absence of the polypeptide conjugate.

In some embodiments, the target antigen is selected from somatostatin 14, gonadotropin releasing hormone (GnRH), luteinizing hormone releasing factor, calcitonin neuropeptide, myostatin, HIV envelope protein, tuberculosis outer membrane protein, *Neisseria* meningitides outer membrane protein complex; or a fragment thereof.

In some embodiments, the target antigen fragment is a polypeptide from 5 to 40 amino acids in length.

In some embodiments, the target antigen comprises an amino acid sequence consisting of one or more of SEQ ID NOs: 1, 32, 33, 34, 35, 36, 37, 38, 40, 41, 43, 44, 46, 47, 48, 49, 50, 51, or 52.

In some embodiments, the target antigen comprises an amino acid sequence consisting of SEQ ID NO: 1.

In some embodiments, the target antigen is not somatostatin 14.

In some embodiments, a method is provided for rapidly increasing milk production in an animal, the method comprising: (1) administering an immunogenic amount of a vaccine to an animal, the vaccine comprising a polypeptide conjugate comprising a target antigen that is somatostatin-14 attached to an inactivated chloramphenicol acetyl transferase (CAT) enzyme by a linker polypeptide, wherein milk production is significantly increased relative to that of a control animal that does not receive administration of said vaccine. In some aspects, the animal is a dairy cow, beef cow, goat, or sow. In some aspects, the milk production is increased within 4 days of the administration of the vaccine. In some aspects, peak milk production is achieved within 8-14 days of the administration of the vaccine. In some aspects, the increase in milk production persists for at least 21 days.

In some embodiments, a method is provided for rapidly increasing lean meat production in an animal, the method comprising: (1) administering an immunogenic amount of a vaccine to the animal, the vaccine comprising (a) a polypeptide conjugate comprising somatostatin-14 covalently attached to an inactivated CAT enzyme by a linker polypeptide, and (2) subsequently administering at least one additional immunogenic amount of the vaccine, wherein subsequent administration does not produce an anamnestic response to the carrier, and wherein lean meat production is increased relative to that of an animal that does not receive said administration.

In some aspects, wherein the vaccine is administered at least 3 times. In some aspects, the vaccine is administered at intervals of 21 days. In some aspects, the animal is a pig or cow.

In some embodiments, a method is provided for developing a conjugated vaccine, comprising selecting a target antigen exhibiting low % predicted B-cell epitopes; and covalently attaching the target antigen to a carrier polypeptide via a linker polypeptide exhibiting high % predicted linear B-cell epitopes to form a polypeptide conjugate; wherein the carrier polypeptide does not stimulate a substantial T cell response. In some aspects, the target antigen exhibits lower % predicted B-cell epitopes than the linker polypeptide. In some aspects, the BepiPred 1.0 predicted Linear B-cell epitope score threshold is 0.2. In some aspects, the linker polypeptide is heterologous to the target antigen.

Figure 1:
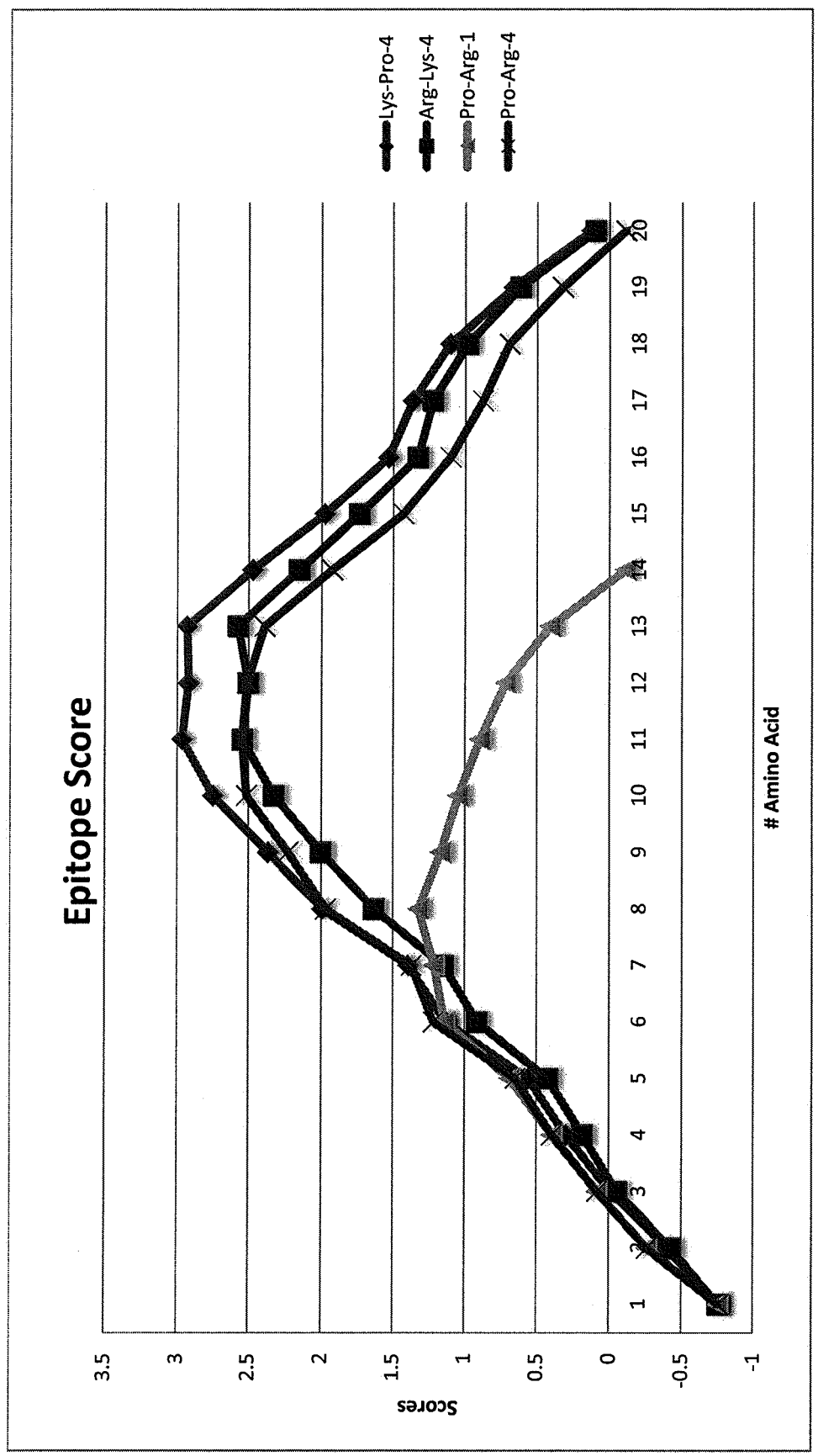
FIG. 1 is a graph showing BepiPred 1.0 predicted linear B epitope scores of four different linker sequences, in accordance with embodiments described herein.
Figure 2:
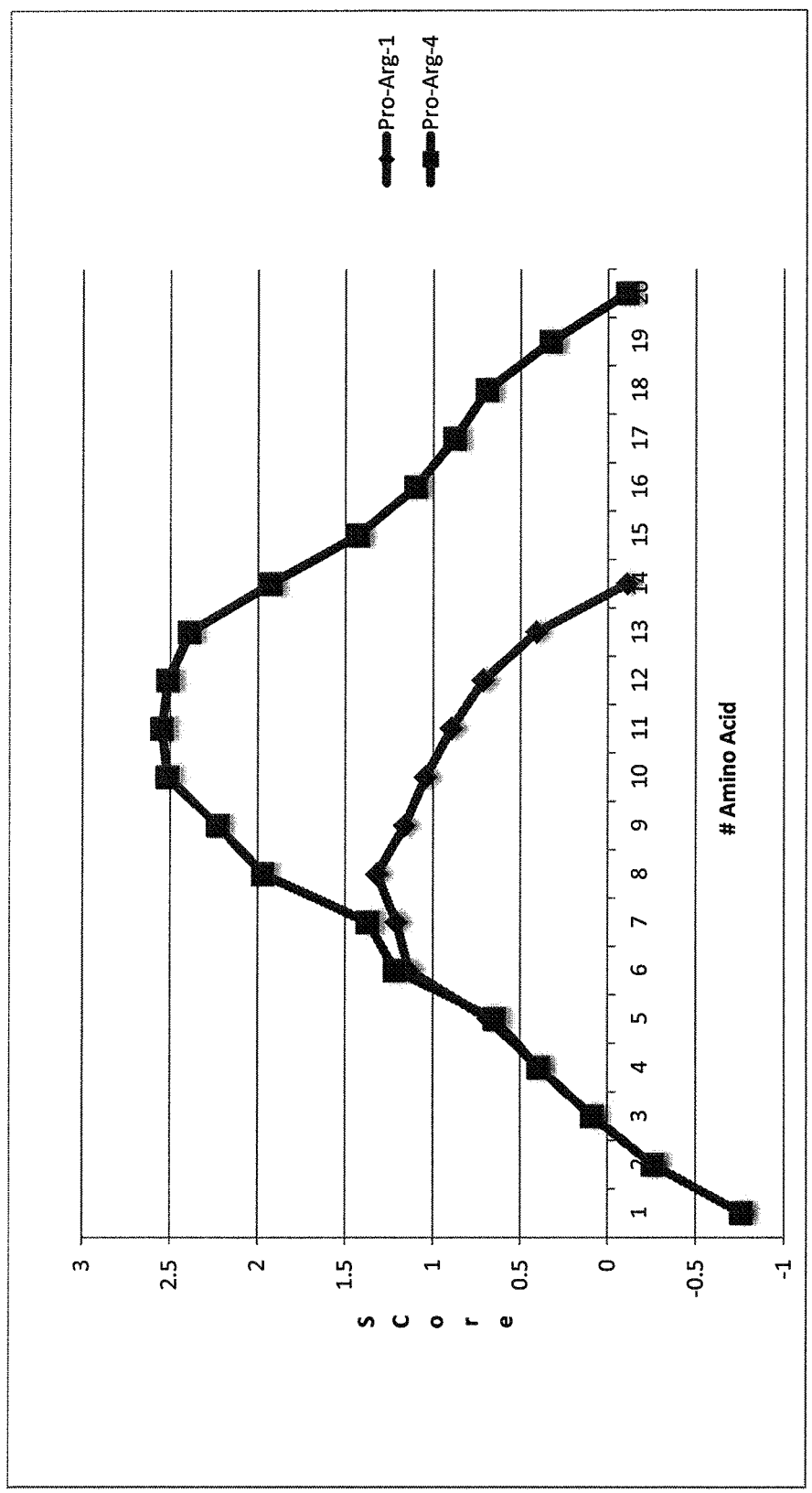
FIG. 2 is a graph showing that the B epitope predicted scores of a linker described herein having four repeated Pro-Arg sequences are higher than for a single Pro-Arg sequence.

IDENTIFICATION OF SEQUENCES AND SEQUENCE IDENTIFIERS cggtgaaaacctggcctatttccctaaagggtttattgagaatatgttttcgtctcagccaatccctgggtgagtttcaccagttttgatttaaac
gtggccaatatggacaacttcttcgccccgttttcaccatgggcaaatattatacgcaaggcgacaaggtgctgatgccgctggcgattcag
gttggtggtgccgtttgtgatggcttccatgtcggccgtatgcttaatgaactgcagcag SEQ ID NO: 3: (His192→Gly, His193→Gly):
mekkitgyttvdisqwhrkehfeafqsyaqctynqtyqlditaflktvkknkhkfypafihilarlmnahpefrmamkdgelviwdsv
hpcytvfheqtetfsslwseyhddfrqflhiysqdvacygenlayfpkgfienmffvsanpwvsftsfdlnvanmdnffapvftmgk
yytqgdkvlmplaiqvggavcdgfhvgrmlnelqq (210 Aas)

SEQ ID NO: 4 (His193→Gly)
atggagaaaaaaatcactggatataccaccgttgatatatcccaatggcatcgtaaagaacattttgaggcatttcagtcagttgctcaatgtac
ctataaccagaccgttcagctggatattacggcctttttaaagaccgtaaagaaaaataagcacaagttttatccggcctttattcacattcttgc
ccgcctgatgaatgctcatccggaattccgtatggcaatgaaagacggtgagctggtgatatgggatagtgttcacccttgttacaccgttttc
catgagcaaactgaaacgttttcatcgctctggagtgaataccacgacgatttccggcagtttctacacatatattcgcaagatgtggcgtgtta
cggtgaaaacctggcctatttccctaaagggtttattgagaatatgttttcgtctcagccaatccctgggtgagtttcaccagttttgatttaaac
gtggccaatatggacaacttcttcgccccgttttcaccatgggcaaatattatacgcaaggcgacaaggtgctgatgccgctggcgattcag
gttcatggtgccgtttgtgatggcttccatgtcggccgtatgcttaatgaactgcagcag SEQ ID NO: 5 (1 His193→Ala)
atggagaaaaaaatcactggatataccaccgttgatatatcccaatggcatcgtaaagaacattttgaggcatttcagtcagttgctcaatgtac
ctataaccagaccgttcagctggatattacggcctttttaaagaccgtaaagaaaaataagcacaagttttatccggcctttattcacattcttgc
ccgcctgatgaatgctcatccggaattccgtatggcaatgaaagacggtgagctggtgatatgggatagtgttcacccttgttacaccgttttc
catgagcaaactgaaacgttttcatcgctctggagtgaataccacgacgatttccggcagtttctacacatatattcgcaagatgtggcgtgtta
cggtgaaaacctggcctatttccctaaagggtttattgagaatatgttttcgtctcagccaatccctgggtgagtttcaccagttttgatttaaac
gtggccaatatggacaacttcttcgccccgttttcaccatgggcaaatattatacgcaaggcgacaaggtgctgatgccgctggcgattcag
gttcatgctgccgtttgtgatggcttccatgtcggccgtatgcttaatgaactgcagcag SEQ ID NO: 6 (1 His + CAT wt)
atggagaaaaaaatcactggatataccaccgttgatatatcccaatggcatcgtaaagaacattttgaggcatttcagtcagttgctcaatgtac
ctataaccagaccgttcagctggatattacggcctttttaaagaccgtaaagaaaaataagcacaagttttatccggcctttattcacattcttgc
ccgcctgatgaatgctcatccggaattccgtatggcaatgaaagacggtgagctggtgatatgggatagtgttcacccttgttacaccgttttc
catgagcaaactgaaacgttttcatcgctctggagtgaataccacgacgatttccggcagtttctacacatatattcgcaagatgtggcgtgtta
cggtgaaaacctggcctatttccctaaagggtttattgagaatatgttttcgtctcagccaatccctgggtgagtttcaccagttttgatttaaac
gtggccaatatggacaacttcttcgccccgttttcaccatgggcaaatattatacgcaaggcgacaaggtgctgatgccgctggcgattcag
gttcatggtgccgtttgtgatggcttccatgtcggcagaatgcttaatgaactgcagcag SEQ ID NO: 7 (one H→G):
mekkitgyttvdisqwhrkehfeafqsvaqctynqtvqlditaflktvkknkhkfypafihilarlmnahpefrmamkdgelviwdsv
hpcytvfheqtetfsslwseyhddfrqflhiysqdvacygenlayfpkgfienmffvsanpwvsftsfdlnvanmdnffapvftmgk
yytqgdkvlmplaiqvhgavcdgfhvgrmlnelqq (210 Aas)

SEQ ID NO: 8: (H→A)
mekkitgyttvdisqwhrkehfeafqsvaqctynqtvqlditaflktvkknkhkfypafihilarlmnahpefrmamkdgelviwdsv
hpcytvfheqtetfsslwseyhddfrqflhiysqdvacygenlayfpkgfienmffvsanpwvsftsfdlnvanmdnffapvftmgk
yytqgdkvlmplaiqvhaavcdgfhvgrmlnelqq (210 Aas)

SEQ ID NO: 9
tgggaactgcaccgttctggtccacgcccgcgccctcgcccacgtccggaattcatg

SEQ ID NO: 10
welhrsgprprprprpefm (19 Aas)

SEQ ID NO: 11
welhrsgprprpefm (15 Aas)

SEQ ID NO: 12
atggagaaaaaaatcactggatataccaccgttgatatatcccaatggcatcgtaaagaacattttgaggcatttcagtcagttgctcaatgtac
ctataaccagaccgttcagctggatattacggcctttttaaagaccgtaaagaaaaataagcacaagttttatccggcctttattcacattcttgc
ccgcctgatgaatgctcatccggaattccgtatggcaatgaaagacggtgagctggtgatatgggatagtgttcacccttgttacaccgttttc
catgagcaaactgaaacgttttcatcgctctggagtgaataccacgacgatttccggcagtttctacacatatattcgcaagatgtggcgtgtta
cggtgaaaacctggcctatttccctaaagggtttattgagaatatgttttcgtctcagccaatccctgggtgagtttcaccagttttgatttaaac
gtggccaatatggacaacttcttcgccccgttttcaccatgggcaaatattatacgcaaggcgacaaggtgctgatgccgctggcgattcag
gttggtggtgccgtttgtgatggcttccatgtcggccgtatgcttaatgaactgcagcagtgggaactgcaccgttctggtccacgcccgcgc
cctcgcccacgtccggaattcatggccggctgcaagaacttcttttggaaaacctttacgagctgc SEQ ID NO: 13
mekkitgyttvdisqwhrkehfeafqsvaqctynqtvqlditaflktvkknkhkfypafihilarlmnahpefrmamkdgelviwdsv
hpcytvfheqtetfsslwseyhddfrqflhiysqdvacygenlayfpkgfienmffvsanpwvsftsfdlnvanmdnffapvftmgk
yytqgdkvlmplaiqv*gg*avcdgfhvgrmlnelqqwelhrsgprprprprpefmagcknffwktftsc (243 Aas)

SEQ ID NO: 14
mekkitgyttvdisqwhrkehfeafqsvaqctynqtvqlditaflktvkknkhkfypafihilarlmnahpefrmamkdgelviwdsv
hpcytvfheqtetfsslwseyhddfrqflhiysqdvacygenlayfpkgfienmffvsanpwvsftsfdlnvanmdnffapvftmgk
yytqgdkvlmplaiqv*hh*avcdgfhvgrmlnelqqwelhrsgprprprprpefmagcknffwktftsc (243 Aas)

-continued

| IDENTIFICATION OF SEQUENCES AND SEQUENCE IDENTIFIERS |
|---|
| SEQ ID NO: 15<br>gctggctgcaagaatttcttctggaagactttcacatcctgt |
| SEQ ID NO: 16<br>welhrsgprprprpefm (17 Aas) |
| SEQ ID NO: 17<br>welhrsgprprprprprpefm (21 Aas) |
| SEQ ID NO: 18<br>welhrsgprprprprprprpefm (23 Aas) |
| SEQ ID NO: 19<br>welhrsgprpefm (13 Aas) |
| SEQ ID NO: 20<br>welhrsgpkpkpkpkpefm (19 Aas) |
| SEQ ID NO: 21<br>welhrsgpkpkpkpefm (17 Aas) |
| SEQ ID NO: 22<br>welhrsgpkpkpefm (15 Aas) |
| SEQ ID NO: 23<br>welhrsgpkpefm (13 Aas) |
| SEQ ID NO: 24<br>welhrsgpkpkpkpkpkpefm (21 Aas) |
| SEQ ID NO: 25<br>welhrsgpkpkpkpkpkpkpefm (23 Aas) |
| SEQ ID NO: 26: (His192→Ala, His193→Ala):<br>mekkitgyttvdisqwhrkehfeafqsvaqctynqtvqlditaflktvkknkhkfypafihilarlmnahpefrmamkdgelviwdsv<br>hpcytvfheqtetfsslwseyhddfrqflhiysqdvacygenlayfpkgfienmffvsanpwvsftsfdlnvanmdnffapvftmgk<br>yytqgdkvlmplaiqvaaavcdgfhvgrmlnelqq (210 Aas) |
| SEQ ID NO: 27: (His192→Ala, His193→Gly):<br>mekkitgyttvdisqwhrkehfeafqsvaqctynqtvqlditaflktvkknkhkfypafihilarlmnahpefrmamkdgelviwdsv<br>hpcytvfheqtetfsslwseyhddfrqflhiysqdvacygenlayfpkgfienmffvsanpwvsftsfdlnvanmdnffapvftmgk<br>yytqgdkvlmplaiqvagavcdgfhvgrmlnelqq (210 Aas) |
| SEQ ID NO: 28: (His192→Gly, His193→Ala):<br>mekkitgyttvdisqwhrkehfeafqsvaqctynqtvqlditaflktvkknkhkfypafihilarlmnahpefrmamkdgelviwdsv<br>hpcytvfheqtetfsslwseyhddfrqflhiysqdvacygenlayfpkgfienmffvsanpwvsftsfdlnvanmdnffapvftmgk<br>yytqgdkvlmplaiqvgaavcdgfhvgrmlnelqq (210 Aas) |
| SEQ ID NO: 29: (His192, His193):<br>mekkitgyttvdisqwhrkehfeafqsvaqctynqtvqlditaflktvkknkhkfypafihilarlmnahpefrmamkdgelviwdsv<br>hpcytvfheqtetfsslwseyhddfrqflhiysqdvacygenlayfpkgfienmffvsanpwvsftsfdlnvanmdnffapvftmgk<br>yytqgdkvlmplaiqvhhavcdgfhvgrmlnelqq (210 Aas) |
| SEQ ID NO: 30 (Linker-SST)<br>welhrsgprprprprpefmAGCKNFFWKTFTSC |

Additional sequences are provided in the Tables herein.

DETAILED DESCRIPTION OF THE INVENTION

Chloramphenicol Acetyl Transferase (CAT)-Defective Somatostatin Fusion Proteins are disclosed in U.S. Pat. Nos. 6,316,004, 7,722,881, 7,943,143, 8,367,073 and 8,425,914; each of which is incorporated herein by reference. Although certain aspects of these fusion proteins were previously disclosed, certain additional aspects of the fusion proteins have now been developed. In addition, a model is provided for developing other polypeptide conjugates exhibiting improved immunogenic response to a low B-cell epitope target antigen in a subject.

In some embodiments, methods are provided to improve an immunological response in a subject to a target antigen, or shorten the time to induce a specific immunological response or effect due to administration of a target antigen in a subject, comprising administering to the subject a polypeptide conjugate comprising a carrier polypeptide, a linker polypeptide and the target antigen, wherein the linker polypeptide exhibits high % predicted linear B-cell epitopes, and wherein the carrier polypeptide does not stimulate a substantial T-cell response. The method is particularly effective for target antigens exhibiting low % predicted linear B-cell epitopes.

The following definitions are provided to facilitate understanding of certain terms used frequently herein and are not meant to limit the scope of the present disclosure.

Definitions:

The term "amino acid" refers to any of the twenty naturally occurring amino acids as well as any modified amino acid sequences. Modifications may include natural processes such as posttranslational processing, or may include chemical modifications which are known in the art. Modifications include but are not limited to: phosphorylation, ubiquitination, acetylation, amidation, glycosylation, covalent attachment of flavin, ADP-ribosylation, cross-linking, iodination, methylation, and the like.

As used herein, the term "epitope" refers to the site on an antigen to which B and/or T cells respond.

As used herein, the term "B-cell epitope" or "B cell epitope" refers to the site of an antigen, such as a protein or other molecule, that is specifically recognized by antibodies (made by B-cells) of the immune system. Knowledge of B-cell epitopes may be used in the design of vaccines and diagnostics tests.

As used herein, the term "improved immunological response" in a subject following immunization with the polypeptide conjugate of the invention refers to one or more of (1) a statistically significant increase in serum anti-target antigen IgG or serum anti-carrier IgG from the subject observed after the first or subsequent immunization with the polypeptide conjugate, compared to control receiving immunization with target antigen and/or carrier without polypeptide conjugation via high predicted % B-cell epitope linker, (2) a statistically significant increase or decrease in a specific effect in the subject in response to administration of the polypeptide conjugate, or (3) a statistically significant faster immunological response compared to a control.

In some embodiments, the specific effect is increased milk production, increased body weight, increased lean body weight, decreased percent body-fat, or decreased body weight in the subject compared to a control without immunization.

In some embodiments, the improved immunological response is measured as a statistically significant increase or decrease in a specific effect response measurement following immunization with the polypeptide conjugate, such as an increase in specific antibody titer, an increase in volume or weight of milk production compared to a control or to the same individual over time, an increase in overall body weight, an increase in lean tissue, or a decrease in body weight.

In some embodiments, the improved immunological response or specific effect is a faster than predicted specific response, wherein the improved immunological response occurs within less than one day, less than two days, less than three days, less than four days, less than five days, less than six days, or less than seven days, post vaccination following the first or subsequent vaccinations with the polypeptide conjugate. In some embodiments, the improved immunological response is a B-cell mediated immunological response.

As used herein, the term "animal" or "subject" or "patient" refers to a vertebrate, typically a mammal, in need of the compositions and/or methods of the present invention, for example, a human, cow, steer, calf, pig, sheep, goat, or horse in need of treatment of one or more disease states; or a production animal, such as a cow, steer, calf, pig, sheep, goat, in need of improved desirable production characteristics.

As used herein, the terms "polypeptide conjugate", or "chimeric polypeptide" refer to a molecule comprising a first target antigen polypeptide covalently attached to a second, heterologous carrier polypeptide, such that the first and second polypeptides are expressed in frame. In some embodiments, the first and second polypeptides are attached via a linker or linker segment to optimize expression and function of the chimeric polypeptide(s) of the invention. In embodiments, the linker polypeptide comprises one or more B-cell epitopes, which allow it to preferentially stimulate a B-cell mediated immune response in the subject. In some embodiments, the polypeptide conjugate is a fusion protein. In other embodiments, the target antigen may be linked covalently to the linker, and/or the linker may be linked to the carrier polypeptide, via chemical means known in the art.

The term "carrier polypeptide" refers to a polypeptide selected for use in the polypeptide conjugate used to increase the molecular weight of a polypeptide conjugate comprising a small molecular weight target antigen, and thus enhance the ability of the subject to raise specific antibodies to the fusion protein and the target antigen. In some embodiments, the carrier polypeptide does not stimulate a substantial T-cell response.

As used herein, the term "linker polypeptide" or "spacer polypeptide" refers to a short polypeptide used to covalently bind the target antigen to the carrier polypeptide. The linker polypeptide is selected to exhibit high % predicted linear B-epitopes, and optionally to position the target antigen on the surface of the polypeptide conjugate, and enhance stability of the polypeptide conjugate.

As used herein, the term "target antigen" refers to any polypeptide antigen of interest. In some embodiments, the target antigen exhibits low % predicted linear B-cell epitopes. A low B-cell target epitope is most likely to benefit from incorporation to a polypeptide conjugate of the invention, particularly in terms of increased immunogenicity.

The term "endotoxin" refers to toxins associated in the cell walls of gram negative bacteria. In some cases the toxins are lipopolysaccharide components of bacterial membranes or components of outer membrane of gram negative bacteria cell walls.

"Like amino acid," as used herein, refers to any amino acid that modifies the domain or epitope shape so as to render the protein inactive, as defined below. In some embodiments, the "like amino acid" is a non-conservative amino acid substitution. Non-conservative amino acid substitutions for His include any non-His amino acid. In some embodiments, non-conservative amino acid substitution for His is selected from Gly, Ala, Val, Leu, or Ile; preferably Gly or Ala. Conservative and non-conservative amino acid replacements are defined in Betts et al., 2003, Amino acid properties and consequences of substitutions, Ch. 14, Bioinformatics for Geneticists, John Wiley & Sons, Ltd., pp. 289-316. Note that in the context of certain embodiments of the invention, like amino acid may refer to all amino acids, as any conformational change may result in inactivation.

"Modular," as used herein, refers to the ability of the carrier composition to generally be paired with any number of potential target antigens, for example a target antigen comprising a low predicted B-cell epitope score, without substantial modification, while maintaining its functionality.

The terms "protein," "peptide," and "polypeptide" are used interchangeably to denote an amino acid polymer or a set of two or more interacting or bound amino acid polymers.

The term "inactivated" means at least 75%, more typically 80%, 85%, 90%, 95% and most typically 96% 97%, 98%, 99%, 100% of an enzyme is rendered incapable of acting functionally in a body or biological system. As such, a substantially inactive CAT enzyme is one that has 75%, 80%, 85%, 90%, 95% 96%, 97%, 98%, 99% or 100% of its activity removed. (CAT activity can be determined using known functional assays, for example binding of n-Butyryl Coenzyme A to radiolabelled chloramphenicol and subsequent measurement by Liquid Scintillation Counting (LCS); by determining the amount of radioactive label transferred from [$^{14}$Cacetyl CoA to chloramphenicol by thin layer chromatography (see Molecular Cloning: A Laboratory Model, 3$^{rd}$ ed., J Sambrook and D W Russell, 2001. Cold Spring Harbor Press] or other known or like assays).

"Treatment" or "treating" refers to improvement of a subject relative to an untreated subject in a relatively identical situation. Treatment or treating generally indicates that a desired pharmacological and/or physiological effect has been achieved using the compositions and methods of the present invention. Treatment or treating can include prophylactic treatments. "Vaccine" refers to any composition that can stimulate the vaccinated subject's immune system to produce antibodies specific for a target antigen for the purposes described herein.

B-Cell Epitope Prediction

As used herein, the term "B cell epitope" or "B-cell epitope" refers to the site of a protein or other molecule that is specifically recognized by antibodies (made by B-cells) of the immune system. Knowledge of B-cell epitopes may be used in the design of vaccines and diagnostics tests.

Most protein B-cell epitopes are composed of different parts of the protein chain brought into proximity by the folding of the protein. These are called "discontinuous epitopes". In about 10% of epitopes, the corresponding antibodies are cross-reactive with a linear peptide epitope that is a fragment of the protein. These epitopes are called "linear epitopes" or "continuous epitopes" made up of a single stretch of the polypeptide chain (a contiguous amino acid sequence).

Traditionally, a peptide fragment scanning method can be employed to identify a B-cell epitope; however, due to high cost and time constraints, this method has limited practical applicability. Prediction methods are much more cost effective.

The classical way of predicting linear B-cell epitopes is by the use of propensity scale methods. These methods assign a propensity value to every amino acid, based on their physico-chemical properties. Fluctuations in the sequence of prediction values are reduced by applying a running average window. Several propensity scale methods exist, for example, as described by Pellequer at al. Pellequer J, Westhof E, Van Regenmortel M: Predicting the location of continuous epitopes in proteins from their primary structure. *Methods Enzymol* 1991, 203:176-201.

Larsen et al. 2006 describe an improved method for predicting linear B-cell epitopes. Larsen tested a variety of prediction models and reported the best single method for predicting linear B-cell epitopes is the hidden Markov model. In order to make more accurate predictions, Larsen combined the hidden Markov model with one of the best propensity scale methods to obtain the BepiPred method. BepiPred 1.0 server predicts the location of linear B-cell epitopes using a combination of a hidden Markov model and a propensity scale model. Jens Erik Pontoppidan Larsen, Ole Lund and Morten Nielsen, "Improved method for predicting linear B-cell epitopes", Immunome Research 2:2, 2006. In some embodiments, prediction of BepiPred 1.0 score for a polypeptide can be performed using an online toolbox, for example, as found at http://tools.immuneepitope.org/bcell/.

In some embodiments, the % predicted linear B-cell epitopes for a polypeptide of interest, for example, a target antigen, carrier polypeptide or a linker polypeptide, is calculated by a method comprising (1) generating a BepiPred 1.0 predicted Linear B-cell epitope score for each amino acid in the amino acid sequence of the polypeptide of interest;
(2) counting the amino acids in the polypeptide of interest for which the BepiPred 1.0 predicted Linear B-cell epitope score is above a threshold value;
(3) dividing the number of amino acids above the threshold value by the total number of amino acids in the polypeptide of interest to get a fraction; and
(4) multiplying the fraction by 100 to get the % predicted Linear B-cell Epitopes for the polypeptide of interest.

In some embodiments, the threshold value for the % predicted linear B-cell epitopes is selected from -0.2, -0.1, 0, 0.1, 0.2, 0.25, 0.3, 0.35, 0.4, 0.5, 0.6, 0.7, 0.8, 0.9, 1.0, 1.1, 1.2, or 1.3. In some embodiments, the threshold is selected from 0.1, 0.2, 0.25, 0.3, or 0.35. In some embodiments, the threshold is 0.2.

Figure 9:
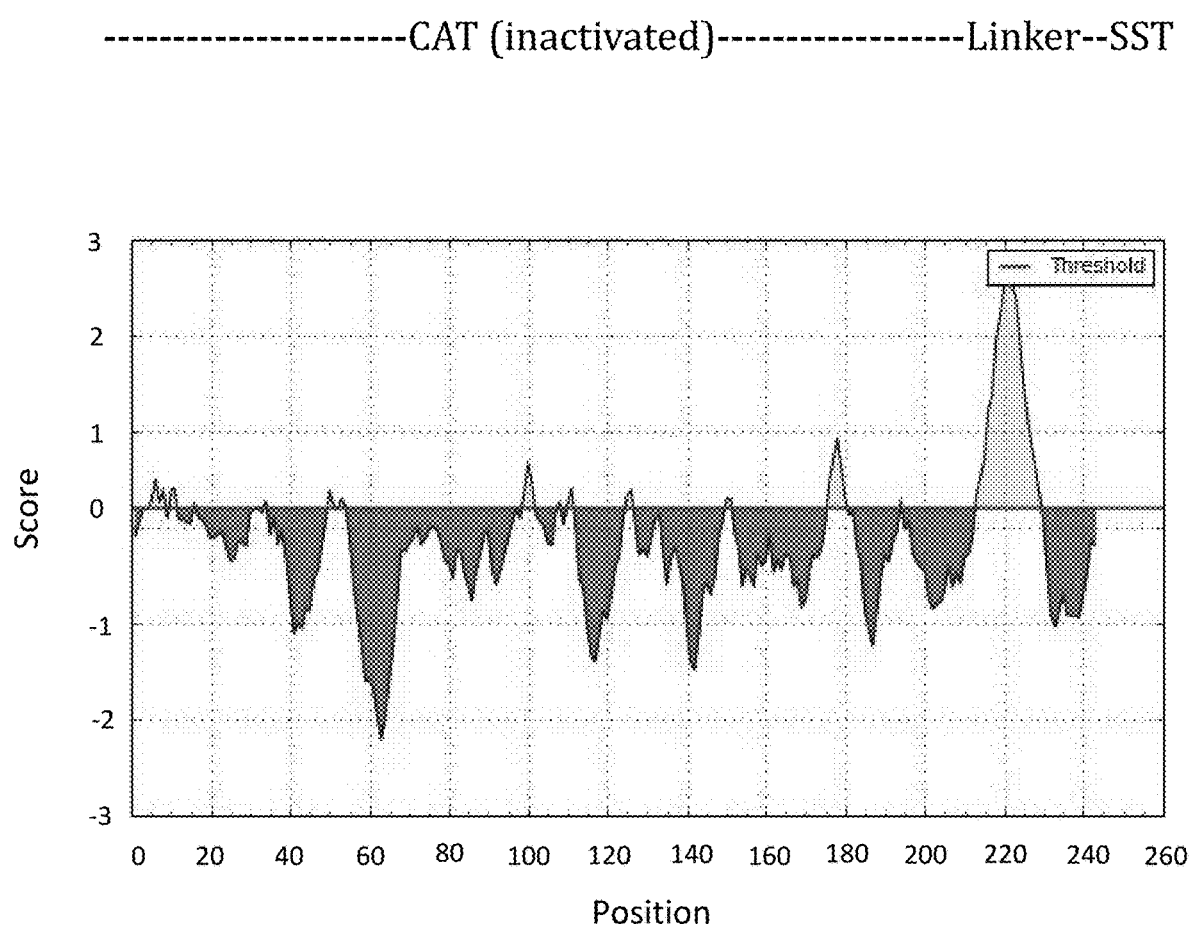

The BepiPred 1.0 method was used herein, as shown in Example 12, to predict B-cell epitopes in a polypeptide conjugate and component target antigen, carrier polypeptide, and linker polypeptides. Model predictions were initially based on amino acid sequences for the polypeptide conjugate disclosed in Chloramphenicol Acetyl Transferase (CAT)-Defective Somatostatin Fusion Protein disclosed in U.S. Pat. Nos. 7,722,881 and 8,425,914, each of which is herein incorporated herein by reference. A graph of the predicted B-cell epitope characteristics along the sequence of the polypeptide conjugate of SEQ ID NO: 13 is shown in FIG. 9 with a threshold of 0.2. The linker portion of the polypeptide conjugate exhibits a high predicted linear B epitope score compared to the carrier (CATinactivated) and the target antigen (SST), as shown in FIG. 9.

Figure 4:
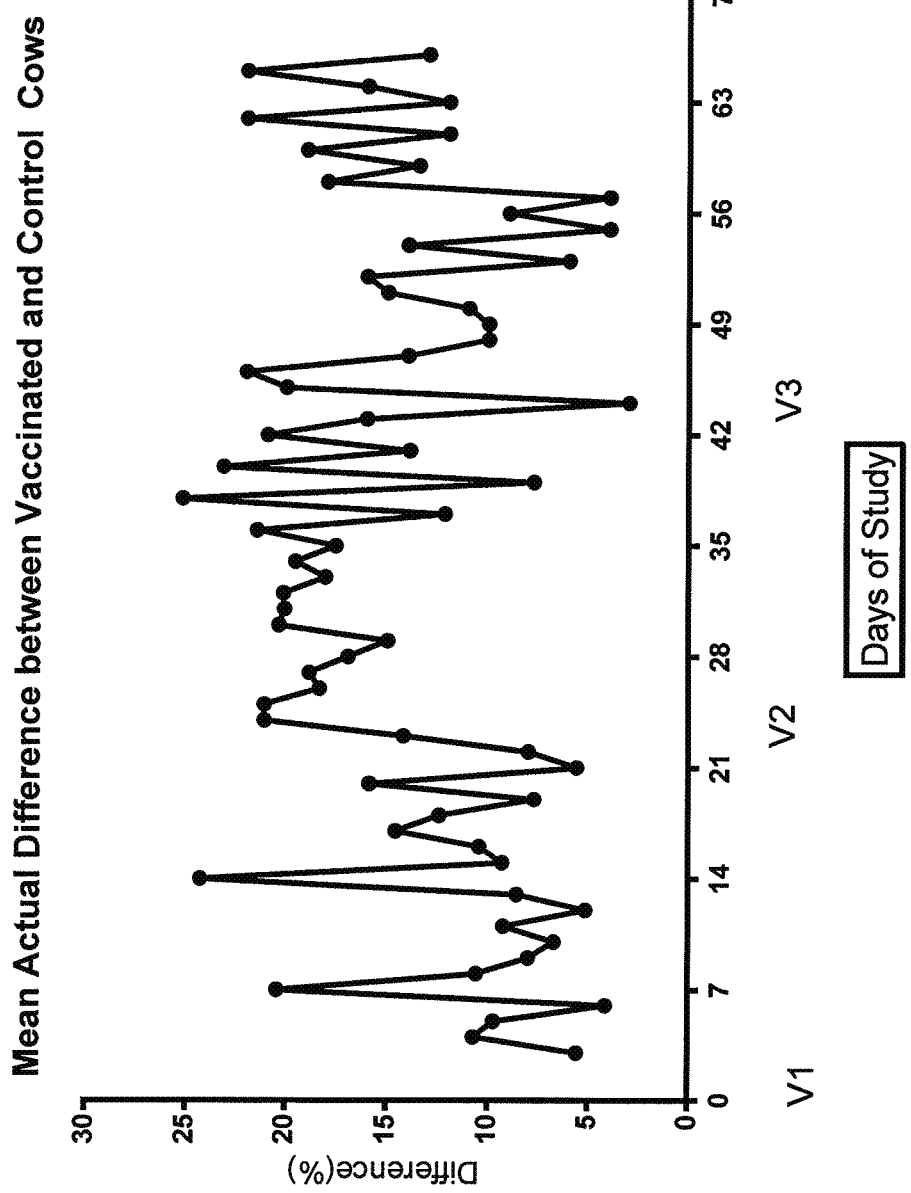

Remarkably, the linker having high % predicted linear B-cell epitopes imparts enhanced B-cell epitope characteristics to the polypeptide conjugate which results in improved immunogenicity of the target antigen, and improved immunological response/effect in the animal following administration, for example, as shown in improved rapid milk production, as shown in FIG. 4.

In one embodiment, a method is provided to enhance the immunogenicity of a target antigen having low predicted linear B-cell epitope scoring, the method comprising attaching covalently a carrier polypeptide to the target antigen by an intervening linker polypeptide to form a polypeptide conjugate, wherein the linker polypeptide exhibits higher predicted linear B-cell epitope scoring than the target antigen.

In one aspect, the target antigen is attached to the linker by a covalent bond selected from an amide bond, a disulfide bond, a urethane bond, a carbonate bond, or an ester bond. In one aspect, the carrier polypeptide is attached to the linker by a covalent bond selected from an amide bond, a disulfide bond, a urethane bond, a carbonate bond, or an ester bond. In one embodiment, the carrier-linker-target antigen is a fusion protein, wherein the covalent bond is an amide bond.

In another embodiment, a method is provided to improve the immunogenicity of a target antigen having low predicted linear B-cell epitope scoring, the method comprising attaching covalently a carrier polypeptide to the target antigen by an intervening linker polypeptide, wherein the linker polypeptide and/or the carrier polypeptide exhibit higher linear B-cell epitope scoring than the target antigen.

In one embodiment, a method is provided to shorten the time to exhibit a specific immune response or effect to a target antigen in a subject following exposure to a vaccine comprising a polypeptide conjugate comprising a target antigen, comprising administering to the subject a polypeptide conjugate comprising the target antigen, a linker polypeptide, and a carrier polypeptide, wherein one or both of the carrier polypeptide and the linker polypeptide exhibit higher predicted linear B-cell epitope scoring than the target antigen. In some aspects, the exposure of the subject to the polypeptide conjugate comprising the target antigen is the first, second, third, fourth, fifth, sixth, or subsequent exposure to the target antigen. In some embodiments, the specific immune response to the target antigen occurs in the subject within a period of six days, five days, four days, three days, two days, one day, or less than one day following exposure to the target antigen.

In one embodiment, a method is provided to shorten the time to exhibit a specific effect of a target antigen in a subject following exposure to the target antigen, comprising administering to the subject a fusion protein comprising the target antigen, a linker polypeptide, and a carrier polypeptide, wherein one or both of the carrier polypeptide and the linker polypeptide exhibit higher predicted linear B-cell epitope scoring than the target antigen. In some aspects, the exposure of the subject to the target antigen is the first, second, third, fourth, fifth, sixth, or subsequent exposure to the target antigen. In some embodiments, the specific effect of the target antigen occurs in the subject within a period of six days, five days, four days, three days, two days, one day, or less than one day following exposure to the target antigen.

Target Antigens:

In some embodiments, the target antigen is selected from any polypeptide antigen of interest, or peptide fragment thereof. In some embodiments, the target antigen or fragment thereof is selected from a peptide fragment of from 5 to 40 amino acids in length. In some embodiments, the target antigen, or fragment thereof, is from 8 to 35 amino acids in length. In some embodiments, the target antigen is from 10 to 25 amino acids in length. In some embodiments, the target antigen, or fragment thereof, is selected from a peptide length that is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acids in length.

In some embodiments, the target antigen exhibits low % predicted linear B-cell epitopes. A low B-cell target epitope is most likely to benefit from incorporation to a polypeptide conjugate of the invention, particularly in terms of increased immunogenicity.

In some embodiments, the target antigen or fragment thereof exhibits low % predicted Linear B-cell Epitopes as calculated by the BepiPred 1.0 method. In some embodiments, the target antigen or fragment thereof exhibits <10%, <7%, <5%, <4%, <3%, <2%, <1%, <0.1% or 0% predicted Linear B-cell Epitopes wherein the % predicted linear B-cell epitopes is determined by BepiPred 1.0 scoring of the target antigen amino acid sequence. Briefly, the amino acid sequence for the target antigen is determined by Bepipred 1.0 scoring as provided herein. The amino acids scored above a threshold value are counted, and divided by the total number of amino acids in the target antigen to get a fractional value. The fractional value is multiplied by 100 to get a % predicted linear B-cell epitope value for the target antigen.

In some embodiments, the target antigen is selected from Gonadotropin Releasing Hormone, Luteinizing Hormone Releasing factor, Calcitonin neuropeptides, Myostatin, HIV envelope protein, Outer membrane Protein (OMP) from pathogenic bacteria (TB. *N. meningitis*); or a target antigen fragment thereof of from 5 to 40 amino acids in length.

In some embodiments, the target antigen is selected from somatostatin 14, a fragment of *Mycobacterium tuberculosis* outer membrane protein A (OmpATb), Gonadotropin Releasing Hormone (GnRH1), a Calcitonin neuropeptide fragment, a myostatin fragment (growth differentiation factor 8; GDF8), a Human Immunodeficiency Virus envelope glycoprotein polypeptide fragment, or a fragment of *Neisseria* meningitides outer membrane protein complex (e.g., Omp85).

In some embodiments, the target antigen is selected from a peptide from 5 amino acids to 40 amino acids in length.

In some embodiments, the target antigen is Somatostatin 14 (SEQ ID NO: 1).

In some embodiments, the target antigen is not Somatostatin 14 (SEQ ID NO: 1).

In some embodiments, the target antigen comprises a fragment of *Mycobacterium tuberculosis* outer membrane protein A (OmpATb). *Mycobacterium tuberculosis* outer membrane protein A (OmpATb) has two functions: as a pore-forming protein with properties of a porin, and in enabling *M. tuberculosis* to respond to reduced environmental pH. The N-terminal domain of OMPATb is required for membrane translocation and pore-forming activity in Mycobacteria. Alahari et al., J Bacteriology 2007, 189(17): 6351-6358. In some embodiments, the target antigen is an OmpATb polypeptide. The amino acid sequence of *M. tuberculosis* H37Rv (GB:AL123456): Rv0899—outer membrane protein A (OmpA Tb) is shown at SEQ ID NO: 31. In some embodiments, the target antigen is selected from a fragment of OmpA Tb exhibiting low % predicted linear B-cell epitopes. In some embodiments, the target antigen is an N-terminal fragment of OmpATb. In some embodiments, the target antigen is selected from one or more of OmpATb fragments OmpATb 32-48 (SEQ ID NO: 32), 75-86 (SEQ ID NO: 33), 104-134 (SEQ ID NO: 34), 235-247 (SEQ ID NO: 35), or 271-289 (SEQ ID NO: 36), 294-302 (SEQ ID NO: 37), or 319-326 (SEQ ID NO: 38), or a fragment thereof.

In some embodiments, the target antigen comprises an amino acid sequence according to Gonadotropin Releasing Hormone (GnRH1), or a fragment thereof. GnRH1 is also known as luteinizing hormone releasing factor, controls a complex process of follicular growth, ovulation, and corpus luteum maintenance in the female, and spermatogenesis in the male. GNRH antagonists block the effects of GnRH and have applications in prostate cancer, fertility treatment, breast cancer, endometriosis, and may be useful in benign prostatic hyperplasia, and as potential contraceptive agents. It is believed that a polypeptide complex will be useful for similar applications. In some embodiments, the target antigen comprises the amino acid sequence of GnRH1, or EHWSYGLRPG, or a fragment thereof. In some embodiments, the target antigen is selected from one or more of GnRH1 fragments GnRH1 1-8 (SEQ ID NO: 40), or GnRH1 1-9 (SEQ ID NO: 41).

In some embodiments, the target antigen comprises an amino acid sequence selected from calcitonin neuropeptide, or a fragment thereof, or preprocalcitonin, or a fragment thereof. Preprocalcitonin is about 139-141 amino acids in length and may exist in more than one isoform. In a specific embodiment, the target antigen has an amino acid sequence corresponding to Calcitonin 85-105, or CGNLSTCMLGTYTQDFNKFHT (SEQ ID NO: 43), a 21 amino acid fragment which exhibits only 4.8% predicted % linear B-cell epitopes.

In some embodiments, the target antigen comprises an amino acid sequence selected from a low B-cell epitope fragment of a member of the calcitonin-like family selected from calcitonin, Calcitinin-Gene Related Peptide, or calcitonin neuropeptide. Calcitonin is a 32 amino acid polypeptide hormone that acts to reduce blood calcium. Calcitonin is used therapeutically for the treatment of osteoporosis. Alternative splicing of the gene coding for calcitonin produces a related peptide called Calcitonin-Gene-Related Peptide (CGRP) is a 37 amino acid vasoactive neuropeptide that is widely distributed in central and peripheral neurons. Ma, Nature and Science 2(3) 2004, 41-47. In humans, two types of CGRP exist-alpha and beta, which differ in sequence by a few amino acids. CGRP induces vasodilatation in a variety of vessels, including the coronary, cerebral and systemic vasculature. CGRP antagonists are being studied for use in treating migraines.

In some embodiments, the target antigen comprises an amino acid sequence selected from a fragment of calcitonin neuropeptide or preprocalcitonin. Preprocalcitonin is about 139-141 amino acids in length and may exist in more than one isoform, for example, as shown in SEQ ID NO: 42. In a specific embodiment, the target antigen has an amino acid sequence corresponding to Calcitonin 85-105, or CGNLSTCMLGTYTQDFNKFHT (SEQ ID NO: 43), a 21 amino acid fragment which exhibits only 4.8% predicted % linear B-cell epitopes. Minvielle et al., JBC 266(36) 24627-31 (1991).

In some embodiments, the target antigen comprises an amino acid sequence selected from an amino acid sequence of myostatin, or a fragment thereof. Myostatin (also known as growth differentiation factor 8; GDF8) is a secreted growth differentiation factor. Animal slacking myostatin have significantly larger muscles. Blocking the activity of myostatin may be of therapeutic benefit in muscle wasting diseases such as muscular dystrophy. Gonzalez-Cavadid et al., 1998, PNAS USA 95, pp. 14938-14943. In some embodiments, the target antigen comprises an amino acid sequence selected from a myostatin fragment selected from 1-20 (SEQ ID NO: 46), 52-68 (SEQ ID NO: 47), 136-162 (SEQ ID NO: 48), 169-179 (SEQ ID NO: 49), 204-216 (SEQ ID NO: 50), 280-302 (SEQ ID NO: 51), 311-329 (SEQ ID NO: 52).

In some embodiments, the target antigen comprises an amino acid sequence selected from a fragment of Human Immunodeficiency Virus envelope glycoprotein amino acid sequence, wherein the fragment exhibits low % predicted linear B-cell epitopes. For example, gp 120 plays a role in the ability of HIV-1 to enter CD4+ cells. Unfortunately, neutralizing antibody responses drive the evolution of HIV-1 envelope during recent infection, therefore additional vaccine constructs are desirable. Frost et al., 2005, PNAS 102(51):18514-18519.

In some embodiments, the target antigen comprises an amino acid sequence selected from a fragment of *Neisseria meningitides* outer membrane protein complex (e.g., Omp85). Omp85 is required for outer membrane protein assembly in gram-negative bacteria and in mitochondria. Volokhina et al., 2009, J Bacteriol, 191(22): 7074-7085.

Table 1 shows % predicted linear B-cell epitopes for certain target antigens and fragments thereof.

TABLE 1

Target Antigens, Fragments and % predicted linear B-cell Epitopes*

| Target Antigen and Fragment Sequences | BepiPred 1.0 Score- No. Aas above threshold (threshold value = 0.2) | Total No. Aas | % Predicted linear B-cell Epitopes | Name |
|---|---|---|---|---|
| AGCKNFFWKTFTSC (SEQ ID NO: 1) | 0 | 14 | 0% | Somato statin 14 |
| MASKAGLGQTPATTDARRTQKF YRGSPGRPW*LIGAVVIPLLIAAIG YG*AFERPQSVTGPTGVLPTLTPT STRGA*SALSLSLLSISR*SGNTVTL IGDFPDEAAK*AALMTALNGLLA PGVNVIDQIHVDPVVRSLD*FSSA EPVFTASVPIPDFGLKVERDTVT LTGTAPSSEHKDAVKRAATSTW PDMKIVNNIEVTGQAPPGPPASG PCADLQSAINAVTGGPIAFGNDG ASLIP*ADYEILNRVAD*KLKACPD ARVTINGYTDNTGSEGIN*IPLSA QRAKIVADYLVARG*VAGD*HIAT VGLGSV*NPIASNATPEGRAKNR RVEIVVN (SEQ ID NO: 31) | 194 | 326 | 60% | *M. tuberculosis* - outer membrane protein A (Omp ATb) |
| *LIGAVVIPLLIAAIGYG* (SEQ ID NO: 32) | 0 | 17 | 0% | OmpA Tb 32-48 |
| *SALSLSLLSISR* (SEQ ID NO: 33) | 0 | 12 | 0% | OmpA Tb 75-86 |
| *AALMTALNGLLAPGVNVIDQIH VDPVVRSLD* (SEQ ID NO: 34) | 0 | 31 | 0% | OmpA Tb 104-134 |

TABLE 1-continued

Target Antigens, Fragments and % predicted linear B-cell Epitopes*

| Target Antigen and Fragment Sequences | BepiPred 1.0 Score- No. Aas above threshold (threshold value = 0.2) | Total No. Aas | % Predicted linear B-cell Epitopes | Name |
|---|---|---|---|---|
| *ADYEILNRVAD* (SEQ ID NO: 35) | 0 | 11 | 0% | OmpA Tb 235-246 |
| *IPLSAQRAKIVADYIVARG* (SEQ ID NO: 36) | 0 | 19 | 0% | OmpA Tb 271-289 |
| *HIATVGLGSV* (SEQ ID NO: 37) | 0 | 10 | 0% | OmpA Tb294-302 |
| *RRVEIVVN* (SEQ ID NO: 38) | 0 | 10 | 0% | OmpA Tb 319-326 |
| pyroGlu-His-Trp-Ser-Tyr-Gly-Leu-Arg-Pro-Gly-NH2<br>EHWSYGLRPG (SEQ ID NO: 39) | 6 | 10 | 60% | GnRH 1-10 |
| EHWSYGLR (SEQ ID NO: 40) | 0 | 8 | 0% | GnRH1 1-8 |
| EHWSYGLRP (SEQ ID NO: 41) | 1 | 9 | 11% | GnRH1 1-9 |
| MGFQKFSPFLALSILVLLQAGSL<br>HAAPFRSALESSPAPATLSEDEA<br>RLLLAALVQNYVQMKASELEQ<br>EQEREGSSLDSPRSKRCGNLSTC<br>MLGTYTQDFNKFHTFPQTAIGV<br>GAPGKKRDMSSDLERDHRPHVS<br>MPQNA (SEQ ID NO: 42) | 72 | 139 | 52% | calcitonin neuropeptide-preprocalcitonin |
| CGNLSTCMLGTYTQDFNKFHT (SEQ ID NO: 43) | 1 | 21 | 4.8% | Calcitonin 85-105 AA |
| RSKRCGNLSTCMLGTYTQDFNK<br>FHTFPQTAIGVGAP (SEQ ID NO: 44) | 17 | 36 | 47% | Calcitonin AA 81-116 |
| *Mqklqlcvyiylfmlivagp*vdlnenseqkenv<br>ekeglcnactwrqntkss***rieaikiqilsklrlet***a<br>pniskdvirqllpkapplrelidqydvqrddssd<br>gsledddyhattetiitmptesdflmqvdgkp***kc<br>cffkfsskiqynkvvkaqlwiylrpv***etpt***tvfvq<br>ilrlikpm***kdgtrytgirslkldmnpgtgiw***qsi<br>dvktvlqnwl***kqpesnlgieikaldenghdlavt<br>fpgpgedglnpflevkvtdtpkrsrrdfgldcde<br>hstes***rccrypltvdfeafgwdwiiapk***rykany<br>cs***gecefvflqkyphthlvhq***anprgsagpcct<br>ptkmspinmlyfngkeqiiygkipamvvdrcg<br>cs (375 Aas) (SEQ ID NO: 45) | 161 | 375 | 43% | myostatin |
| *Mqklqlcvyiylfmlivagp* (SEQ ID NO: 46) | 0 | 20 | 0% | Myostatin 1-20 |
| *Rieaikiqilsklrlet* (SEQ ID NO: 47) | 0 | 17 | 0% | Myostatin 52-68 |
| *Kccffkfsskiqynkvvkaqlwiylrpv* (SEQ ID NO: 48) | 0 | 28 | 0% | Myostatin 136-162 |
| *Tvfvqilrlikpm* (SEQ ID NO: 49) | 0 | 13 | 0% | Myostatin 169-179 |
| *Qsidvktvlqnwl* (SEQ ID NO: 50) | 0 | 13 | 0% | Myostatin 204-216 |

TABLE 1-continued

Target Antigens, Fragments and % predicted linear B-cell Epitopes*

| Target Antigen and Fragment Sequences | BepiPred 1.0 Score- No. Aas above threshold (threshold value = 0.2) | Total No. Aas | % Predicted linear B-cell Epitopes | Name |
|---|---|---|---|---|
| *Rccrypltvdfeafgwdwiiapk* (SEQ ID NO: 51) | 0 | 23 | 0% | Myostatin 280-302 |
| *Gecefvflqkyphthlvhq* (SEQ ID NO: 52) | 0 | 19 | 0% | Myostatin 311-329 |

Note:
regions of low predicted linear B cell epitope characteristics are shown in italics in some target antigens and fragments in Table 1.

In some embodiments, the target antigen in the carrier-linker-target antigen fusion protein is not somatostatin-14. In other embodiments, the target antigen in the carrier-linker-target antigen fusion protein comprises the somatostatin-14 amino acid sequence of SEQ ID NO: 1.

In some embodiments, the target antigen is Somatostatin-14 (SST). SST is known to have strong inhibitory effect on a large number of hormones involved in the growth and utilization of food in animals. As previously described, for example, in U.S. Pat. No. 7,722,881, chimeric versions of somatostatin were used for immunization of animals that subsequently exhibited an increase in daily weight gain or an increase in milk production.

Linker Polypeptides

Linker polypeptides according to the invention are selected or designed by determining a high B cell epitope score for the peptide. In some embodiments, the B cell epitope scoring system is BepiPred 1.0, as provided herein. In some embodiments, the linker polypeptide exhibits higher predicted linear B-cell epitope scoring than the target antigen.

In some embodiments, the linker polypeptide exhibits >50%, >60%, >70%, >80%, >90%, >95% or >99% predicted linear B-cell epitopes, wherein the % predicted linear B-cell epitopes is determined by (1) generating a BepiPred 1.0 predicted Linear B-cell epitope score for the amino acid sequence of the linker polypeptide, (2) dividing the Bepiprep 1.0 predicted Linear B-cell epitope score by the number of amino acids in the linker polypeptide and (3) multiplying the resulting number by 100 to get the % predicted Linear B-cell Epitopes, as provided herein. In some embodiments, the linker polypeptide exhibits >80%, >90% or >95% predicted linear B-cell epitopes.

In some embodiments, the linker polypeptide is a peptide of 5 to 35 amino acids in length, 8 to 30 amino acids in length or 10 to 25 amino acids in length.

In some embodiments, the linker polypeptide is selected from B cell epitope known in the art. In some embodiments, the linker polypeptide comprises an amino acid sequence selected from linker polypeptide selected from SEQ ID NO: 10, 11, 16, 17, 18, 19, 20, 21, 22, 23, 24, 25, 53, 54, 55, 56 or 57. In some embodiments, the linker polypeptide comprises an amino acid sequence that exhibits 90% or greater, or 95% or greater, sequence identity with an amino acid sequence selected from SEQ ID NO: 10, 11, 16, 17, 18, 19, 20, 21, 22, 23, 24, 25, 53, 54, 55, 56 or 57.

Example linker polypeptides and linear B cell epitope scoring are shown in Table 2.

TABLE 2

Linker Polypeptides with High Linear B Cell Epitope Scoring

| SEQ ID NO: | Linker Polypeptide Sequence | BepiPred 1.0 Score*-No. Aas above threshold of 0.2 | Total No. Aas | % Predicted linear B-cell Epitopes | Source |
|---|---|---|---|---|---|
| 10 | welhrsgprprprprpefm | 16 | 19 | 84% | U.S. Pat. Nos. 7,722,881; 8,425,914; or 2013/0149332 |
| 11 | welhrsgprprpefm | 12 | 15 | 80% | U.S. Pat. Nos. 7,722,881; 8,425,914; or 2013/0149332 |
| 16 | welhrsgprprprpefm | 14 | 17 | 82% | U.S. Pat. Nos. 7,722,881; 8,425,914; or 2013/0149332 |
| 17 | welhrsgprprprprprpefm | 18 | 21 | 86% | U.S. Pat. Nos. 7,722,881; 8,425,914; or 2013/0149332 |

TABLE 2-continued

| SEQ ID NO: | Linker Polypeptide Sequence | BepiPred 1.0 Score*-No. Aas above threshold of 0.2 | Total No. Aas | % Predicted linear B-cell Epitopes | Source |
|---|---|---|---|---|---|
| | Linker Polypeptides with High Linear B Cell Epitope Scoring | | | | |
| 18 | welhrsgprprprprprprpefm | 20 | 23 | 87% | U.S. Pat. Nos. 7,722,881; 8,425,914; or 2013/0149332 |
| 19 | welhrsgprpefm | 10 | 13 | 77% | U.S. Pat. Nos. 7,722,881; 8,425,914; or 2013/0149332 |
| 20 | welhrsgpkpkpkpkpefm | 16 | 19 | 84% | U.S. Pat. Nos. 7,722,881; 8,425,914; or 2013/0149332 |
| 21 | welhrsgpkpkpkpefm | 14 | 17 | 82% | U.S. Pat. Nos. 7,722,881; 8,425,914; or 2013/0149332 |
| 22 | welhrsgpkpkpefm | 12 | 15 | 80% | U.S. Pat. Nos. 7,722,881; 8,425,914; or 2013/0149332 |
| 23 | welhrsgpkpefm | 10 | 13 | 77% | U.S. Pat. Nos. 7,722,881; 8,425,914; or 2013/0149332 |
| 24 | welhrsgpkpkpkpkpkpefm | 18 | 21 | 86% | U.S. Pat. Nos. 7,722,881; 8,425,914; or 2013/0149332 |
| 25 | welhrsgpkpkpkpkpkpkpe fm | 20 | 23 | 87% | U.S. Pat. Nos. 7,722,881; 8,425,914; or 2013/0149332 |
| 53 | PPKDTNQTQPATQPA | 15 | 15 | 100% | Etz et al., 2002, PNAS 99(10): 6673; FIG. 5, *Staphylococcus aureus* synthetic peptide B-cell epitope (LPX-TGp5 epitope) |
| 54 | QGPGAPQGPGAPQGP GAP | 18 | 18 | 100% | *Plasmodium yoelii* circumsporozoite (CS) protein B cell epitope (PyCS-B epitope3) Shiratsuchi et al., 2010, J. Clin. Investigation 120(10): 3688-3701 |
| 55 | QGPGAPQGPGAP | 12 | 12 | 100% | PyCS-B epitope2 |
| 56 | QGPGAPQGPGAPQGP GAPQGPGAP | 24 | 24 | 100% | PyCS-B epitope4 |

TABLE 2-continued

Linker Polypeptides with High Linear B Cell Epitope Scoring

| SEQ ID NO: | Linker Polypeptide Sequence | BepiPred 1.0 Score*-No. Aas above threshold of 0.2 | Total No. Aas | % Predicted linear B-cell Epitopes | Source |
|---|---|---|---|---|---|
| 57 | EHKYSWKS | 8 | 8 | 100% | Dengue Virus Type 1 B cell epitope; (DEN-1 peptide) Wu et al., 2001 J. Clin. Microbiol. 39(3): 977 dren, growth deficiency in adults, lack of adequate endogenous growth hormone secretions, healing of burns, obesity, cardiac disease, etc. In some embodiments, the vaccines described herein are designed for optimal use in vertebrates, particularly humans, and provide for enhanced primary immunogenicity with the absence or limitation of an anamnestic response. Conjugated vaccine embodiments herein are useful with other antigen combinations beyond those useful in the treatment of a target disease state, and may be combined with any suitable target antigen (in the absence of a carrier). Additional novel stand-alone embodiments are therefore within the scope of the present invention.

With regard to somatostatin, vaccines are provided that result in immunogenicity against somatostatin that results in diminution of somatostatin and thereby removal of a proportion of the inhibition that somatostatin exerts on growth hormone release and thereby insulin-like growth factor 1 release. Vaccine embodiments herein are optimized for both safety and function, having highly immunogenic somatostatin constructs in safe and highly effective adjuvant compositions. Vaccines of the present invention require relatively smaller amounts of antigen (as compared to conventional vaccines), have enhanced storage life, and are lower cost. In some embodiments, somatostatin-based vaccines of the invention do not cause an anamnestic response, and may be administered routinely and with increased safety.

In some embodiments, the carrier is selected from a protein selected from a bacterial chloramphenicol acetyl transferase (CAT) polypeptide, an inactivated chloramphenicol acetyl transferase (CAT) polypeptide with a C-terminal deletion, an inactivated chloramphenicol acetyl transferase (CAT) with one or more amino acid substitutions, a beta-galactosidase, a dihydrofolate reductase, or a hydrophobic synthetic polypeptide. In some embodiments, the carrier polypeptide is selected from an inactivated chloramphenicol acetyl transferase (CAT) or a dihydrofolate reductase (DHFR). In some embodiments, the carrier polypeptide does not stimulate a substantial T-cell response.

In some embodiments, the carrier polypeptide is a chloramphenicol acetyl transferase (CAT) polypeptide. CAT is a bacterial enzyme that detoxifies the antibiotic chloramphenicol and is responsible for chloramphenicol in bacteria. The enzyme attaches an acetyl group from acetyl co-A to chloramphenicol which prevents chloramphenicol from binding to ribosomes. A histidine residue located in the C-terminal portion of the enzyme is said to be responsible for the catalytic mechanism. In some embodiments, the carrier polypeptide is a CAT enzyme sequence.

In some embodiments, the carrier polypeptide is a CAT enzyme that is at least partially inactivated by truncation of the polypeptide at the C-terminus and or replacement of one or both of the His residues in the catalytic site. In some aspects, the CAT enzyme is at least partially inactivated by replacement of the His residues at position 192, 193 in the catalytic site of the enzyme.

In some embodiments, the carrier polypeptide is an inactivated chloramphenicol acetyl transferase (CAT) polypeptide selected from SEQ ID NOs: 3, 7, 8, 26, 27, 28 or 29. In some embodiments, the carrier polypeptide is SEQ ID NO: 3.

Novel Vaccine Embodiments for Use in Treatment of Disease

The methods of the invention include the use of a vaccine comprising a polypeptide conjugate such as a fusion protein comprising a target antigen conjugated to a carrier polypeptide that is an inactivated CAT enzyme via a linker that exhibits higher predicted linear B-cell epitope scoring than the target antigen. The carrier is attached to a target antigen via a linker, and the polypeptide conjugate is capable of generating an immune response against the target antigen and similar proteins, while directly targeting B cell epitopes. In some embodiments, neither the target antigen, the linker, nor the carrier polypeptide, stimulate a substantial T-cell response. Administration of the polypeptide conjugate such as a fusion protein to a subject results in a desirable B-cell mediated immune response against the carrier, linker and target antigen, but avoids the development of T-cell memory, limiting recognition and neutralization of the construct by the immune system upon subsequent administrations.

In further embodiments, vaccines comprising the polypeptide conjugate are utilized in a secondary or booster vaccination in a prime-boost vaccine. Using the compositions of the invention as a secondary or booster vaccination has the advantage of allowing further beneficial treatment of a disease state by generating an immune response, without generating a significant T-cell mediated response.

In some embodiments, the target antigens are recombinant proteins typically having truncated or modified sequences, allowing attachment to the linker while maintaining the immunogenicity of the unmodified protein. For example, a protein may be shortened by one or more C- or N-terminal amino acids to allow attachment to the linker.

In some embodiments, the carrier polypeptide is an inactivated CAT provided by the following nucleic acid constructs that encode an inactive CAT enzyme that is without 10 C-terminal amino acids. In some embodiments, the carrier polypeptide CAT construct comprises one or two histidine amino acid modifications therein which result in partial to complete CAT inactivation. In one embodiment, the CAT enzyme is inactivated by removing the imidazole group of His193 (His195 in the canonical $CAM_{III}$ variant) and replacing with a non-conservative amino acid replacement. In another embodiment the CAT enzyme is inactivated by removing the imidazole groups of both His 193 and the nearby His192 (respectively His195 and His194 for $CAT_{III}$ and replacing with a non-conservative amino acid replacement. Removal of the essential His193 (His195 in CATO imidazole group from the active site of CAT and replacement with an alanine, glycine or other non-conservative amino acid results in substantial inactivation of the CAT enzyme (see for example, Lewendon A et al. (1994) Replacement of catalytic histidine-195 of chloramphenicol acetyl transferase: evidence for a general base role for glutamate. Biochemistry. 33(7):1944-50; White et al., (2000) Characterization of Chloramphenicol and Florfenicol Resistance in *Escherichia coli* associated with Bovine Diarrhea. J. Clin. Micro 38(12) p 4593-4598, each of which is incorporated by reference herein for all purposes). In some embodiments, the carrier peptide is an inactivated CAT enzyme comprising a removal of the imidazole group of His192 alone (His 194 for $CAT_{111}$) and replacement with an alanine, glycine or other non-conservative amino acid substitution.

In some aspects, the one or more replaced histidine amino acids are encoded by nucleic acids located at position numbers 574-576 and 577-579 of SEQ ID NO: 2 (corresponding to amino acid numbers 192 and 193 in SEQ ID NO: 3). In some embodiments the nucleic acid sequences of the invention include SEQ ID NO: 4, SEQ ID NO: 5 and SEQ ID NO: 6. Chimeric proteins of the invention that include the histidine replaced constructs herein provide highly immunogenic proteins with little or no CAT activity. The inactivated CAT enzyme embodiments are attached to a target antigen. This attachment is made via linker embodiments, as described more fully below.

CAT inactivation, at sites his192 and/or his193, can be accomplished via any number of known procedures to those skilled in the art including site-directed mutagenesis and synthetic gene assembly. In one embodiment, the nucleic acid sequence that encodes histidine 192 or histidine 193 are modified to encode an alanine, glycine or other like amino acid. In another embodiment, the nucleic acid sequences that encode both histidine 192 and 193 are modified to encode alanine, glycine or other like amino acids. In some embodiments, the carrier polypeptide is an inactivated CAT enzyme comprising amino acid substitutions for both the 192 and 193 histidines selected from the group consisting of alanine, alanine; alanine, glycine; glycine, alanine; and glycine, glycine, at the 192 and 193 position, respectively.

In some embodiments, the carrier polypeptide is a CAT deficient polypeptides, having an amino acid sequence selected from the group consisting of SEQ ID NO: 3, 7, and 8 (corresponding to his→gly at both 192 and 193, his→gly at 193, and his→ala at 193).

The realization that the inactivated CAT enzyme carrier and linkers could present various target antigens such as recombinant proteins in the treatment of diseases or conditions herein without creating an anamnestic response was an unexpected finding of the inventors. Previous vaccine carriers and linkers trigger a normal immune response characterized by T cell response, processing, and a resulting immunological memory for a vaccine. This response may result in neutralization upon subsequent vaccinations, limiting the safety and effectiveness of future administrations of the vaccine. As such, the realization, development, and use of the B-epitope containing carrier and/or linkers of the invention, for use with target antigens exhibiting low B-epitope characteristic, with a reduced anamnestic response, is desired, representing a significant improvement over existing vaccines.

Note that these "carrier" related improvements of CAT for use with small molecules are discussed in co-pending and related U.S. Patent Application S/N PCT/US08/68195 as well as in U.S. Pat. No. 6,316,004 both of which are incorporated by reference herein for all purposes. In particular, the inventors herein unexpectedly found that an inactivated CAT enzyme as a carrier protein for low B epitope-containing target antigens such as recombinant proteins could avoid the significant health risks associated with the enzyme while utilizing the chimeric proteins enhanced capacity for immunogenicity, resistance to enzyme degradation, increased half-life and enhanced uptake by the patient's macrophages.

In some embodiments, a polypeptide conjugate is provided comprising a substantially inactivated CAT enzyme covalently attached to a target antigen via a linker, wherein the linker allows for presentation of the target antigen on a global surface of the fusion protein. Linker embodiments also provide for optimal protease resistance and for optimal epitope exposure. Inclusion of the linker in polypeptide conjugates has resulted in unexpected improvement over constructs not having the linker sequence(s) of the present invention.

In some embodiments, the immunogenic response to a target antigen is a B-cell mediated immunogenic response.

In some embodiments, the polypeptide conjugate is a fusion protein.

See Table 2, showing % predicted Linear B-cell Epitopes for linker polypeptides. Surprisingly, it has been found that the linker of SEQ ID NO: 3 exhibiting >50%, >60%, >70% or preferably >80% predicted Linear B-cell Epitopes imparts the polypeptide conjugate with improved immunological response in a subject.

Further, these chimeric constructs show enhanced storage stability as compared to a target antigen recombinant protein alone. In addition, the polypeptide conjugates of the present invention provide for greater half-life in the patient of the target antigen given the enhanced resistance to degradation in these materials, especially as compared to recombinant proteins with KLH, tetanus toxoids or CRM.

Embodiments of the invention also provide novel adjuvant compositions for enhanced induction of humoral immunity in a target patient. These adjuvant compositions provide a significant improvement over conventional materials for the induction of a humoral response and are safe for use in human targets. Adjuvant compositions herein are used with recombinant protein-based antigens to produce vaccines of the invention. Vaccines of the invention are then useful in the treatment of numerous diseases or conditions.

In embodiments herein, all components of adjuvant compositions are of non-animal origin, thereby eliminating potential cross-contamination of vaccinated humans from potentially contaminated adjuvant components. For example, embodiments herein can utilize animal origin free Tween 80. Surprisingly, animal origin free Tween 80 shows significantly better results in the use of vaccines herein as compared to animal origin Tween 80, and eliminates the possibility of animal-based contamination into the vaccine, e.g., Bovine Spongiform Encephalopathy (BSE). In addition, animal origin free Tween 80 shows better capacity to emulsify as compared to animal origin Tween 80, providing an additional unexpected benefit for its use in accordance to embodiments herein.

Adjuvant embodiments herein are also free of benzene and other like carcinogenic compounds. These embodiments provide a safety benefit not available in most conventional adjuvant compounds. For example, embodiments herein utilize Carbopol 974P or benzene free polycyclic acid.

In one embodiment, the immunologic adjuvant comprises a carbopol base, a squalene base and an arabinogalactan solution. In more detail, the Carbopol base is prepared using Carbopol 974P in water or saline. The squalene base is prepared from a combination of squalene, non-animal origin Tween 80 and Span 85. In some embodiments the squalene base is MF59 (Chiron Corp., Emeryville, Calif.). The arabinogalactan is dissolved in PBS or saline. Adjuvant compositions are combined with chimeric polypeptides of the invention to produce vaccines of the invention.

In yet another embodiment, the immunologic adjuvant comprises a Carbopol base, a squalene base and a tragacanthin solution. In more detail, the Carbopol base is prepared using Carbopol 974 P in water or saline. The squalene base is prepared from a combination of squalene, non-animal origin Tween 80 and Span 85. Purified tragacanthin is dissolved in PBS or saline. Adjuvant compositions are combined with chimeric polypeptides of the invention to produce vaccines or the invention.

Specific adjuvant combination and concentrations are shown in the examples below. Adjuvants in accordance with the present invention are safe and effective for human use, avoid animal products, avoid petroleum based hydrocarbons, and avoid carcinogenic compounds.

Vectors and Host Cells

The present invention also relates to vectors comprising the polynucleotide molecules of the invention, as well as host cells transformed with such vectors. Any of the polynucleotide molecules of the invention may be joined to a vector, which generally include a selectable marker and origin of replication, for the propagation host of interest. Host cells are genetically engineered to include these vectors and thereby express the polypeptides of the invention. Generally, vectors herein include polynucleotides molecules of the invention operably linked to suitable transcriptional or translational regulatory sequences, such as those for microbial or viral host cells. Examples of regulatory sequences include transcriptional promoters, operators, or enhancers, mRNA ribosomal binding sites, and appropriate sequences which control transcription and translation. Nucleotide sequences are operably linked when the regulatory sequences herein functionally relate to the chimeric polypeptide encoding polynucleotides of the invention.

Typical vehicles include plasmids, yeast shuttle vectors, baculovirus, inactivated adenovirus, and the like. In one embodiment the vehicle is a modified pET30b CatSom plasmid. Target host cells for use herein include bacterial host, e.g., E. coli, yeast, SF-9 insect cells, mammalian cells, plant cells, and the like.

In one embodiment, the regulatory sequences include a T7lac, CAT, Trp, or T5 promoter for expression of the chimeric polypeptides of the invention in E. coli or other like microbes. These regulatory sequences are known in the art and are used under appropriate and known conditions.

Where genetically modified green plant cells are utilized for expression, systems as developed by Planet Biotechnology and others can be utilized.

Various plasmids of the invention have been constructed for expression of chimeric polypeptides of the invention through utilization of target regulatory sequences. Illustrative plasmids can include a T7lac promoter.

Host cells for expression of target chimeric polypeptides include prokaryotes, yeast and higher eukaryotic cells. Illustrative prokaryotic hosts include bacteria of the genera Escherichia, Bacillus, and Salmonella as well as the genera Pseudomonas and Streptomyces. In typical embodiments the host cell is of the genera Escherichia and can be Escherichia coli (E. coli).

As shown in the Examples below, constructs of the invention provide for optimal CAT deficient recombinant-protein expression under a variety of conditions. These constructs are particularly efficient for expression in prokaryotic hosts and in particular bacteria of the genera Escherichia. Note as well that various plant expression systems can also be used in the context of the present invention, typically using Agrobacterium trameficies.

Endotoxin Free Fusion Protein Purification

Aspects of the present invention include use of endotoxin free, codon-optimized, CAT-deficient recombinant-protein for use in vaccination of animals, and in particular for vaccination of farm animals, which in some cases are United States bred dairy cows. Endotoxin free materials are particularly important for cattle bred and raised in the United States (see for example, Drackley, J K 2004. Physiological adaptations in transition dairy cows. Pp 74-87 in Proc. Minnesota Dairy Herd Health Conf., St Paul, Minn. University of Minnesota, St. Paul). Also, because the methods contemplated herein include repeated vaccinations in animals, including humans, endotoxin free compositions are of increased importance.

In one embodiment, the chimeric immunogenic recombinant protein-comprising proteins of the invention are prepared by transforming target cells with appropriate recombinant protein-containing vehicles. As noted above, vehicles for use herein include known plasmid and vector systems suitable for expression in selected target cells.

In an aspect of the invention, chimeric immunogenic recombinant protein-comprising proteins are expressed in target host cells. Chimeric protein expression is performed using target regulatory sequences. In some aspects the chimeric polypeptides have been optimized (especially with regard to linker sequences disclosed herein) for expression in E. coli.

Chimeric protein can then be purified in accordance with known protein purification technologies, including, for example, lysozyme lysis, differential centrifugation of inclusion bodies, sieve chromatography and the like. Refolding procedures can be conducted in guanidine chloride and urea at alkaline pH followed by dialysis and lyophilization.

In one embodiment, E. coli cells are transformed using a codon-optimized, CAT-deficient recombinant-protein containing plasmid, the plasmid having appropriate E. coli base regulatory sequences for expression. In some cases, fermentation of approximately ten liters of these cells provides at least 500 grams and in some cases 600 grams of total biomass, yielding about 4-6 grams of total protein. It is estimated from silver and coomassie blue staining that up to half of the protein can be chimeric protein (not shown).

In some embodiments herein, chimeric protein of the invention is purified from transformed host cells in a substantially endotoxin free state. Realization that endotoxin, and in particular multiple exposures to endotoxin, in some animals, and in particular dairy cows, results in substantially compromised animals (mastitis and endotoxin shock in dairy cows bred and raised in the United States) was an unexpected and surprising result that the present inventors obtained. This realization resulted in an attempt to remove or lower the endotoxin dose amount or number of exposures in dairy cow vaccinations. Note that this endotoxin based effect is much less realized in cows bred and raised in Russia and other countries as the dairy cattle are descendent from a different strain of cow (Holstein Association, 1 Holstein Place, Brattleboro, Vt. 05302-0808). This finding in United States dairy cows is generally contrary to the expectation that a vaccine should include some low amount of endotoxin to help maximize an animals' immune response, as is the case for dairy cows when vaccinated with somatostatin in some other European markets (see U.S. Pat. No. 6,316,004).

As such, some embodiments herein are directed to production of substantially endotoxin free chimeric proteins for use in vaccines, and especially for use in vaccines used in the cattle industry and used in the cattle industry within the United States. In certain embodiments the endotoxin levels are at or below 1 EU/ml and in other embodiments the endotoxin levels are substantially eliminated, i.e., the chimeric polypeptides of the invention are substantially endotoxin free.

In one embodiment, recovered IP from lysed host cells is washed multiple times using a wash solution devoid of endotoxin, i.e., endotoxin free water or solution. The recovered IP pellet can optionally be washed until endotoxin levels are below approximately 1 EU/ml (endotoxin tests can be performed using one or more known assays, including commercially available test kits from MP Biochemicals, Charles River, etc.). In some embodiments the wash solution is endotoxin free and includes one or more proteolytic protein inhibitor(s), e.g., phenylmethanesulphonylfluoride (PMSF), 4-(2-aminoethyl)-benzenesulphonyl fluoride (AEBSF), etc. In some embodiments the wash solution is phosphate buffered saline (PBS) having an inhibitory effective amount of PMSF, AEBSF or a combination of both PMSF and AEBSF.

In some aspects, substantially endotoxin free pellets can be treated with a protein unfolding solution at pH 12.5 containing urea and refolded in a protein refolding solution containing a reduced molarity of urea with arginine, glycerol and/or sucrose. Purified chimeric protein concentration is modified to be between 1 and 3 mg/ml and typically about 1.4 to 1.8 mg/ml. In some cases, substantially endotoxin free chimeric protein is provided to vaccine formulations at about 1.5 to 5 mg/2 ml dose and more typically from 2.0 to 3.5 mg/2 ml dose.

Other endotoxin removal procedures are envisioned to be within the scope of the present invention and can include, for example, commercially available ion-exchange endotoxin removal columns, hydrophobic columns, etc (see for example Mustang E or G Columns (Millipore)).

Enhanced Immune Response Adjuvant

Embodiments of the invention provide new adjuvants for enhanced induction of humoral immunity, or the aspect of immunity that is mediated by macromolecules found in extracellular fluids, such as secreted antibodies and antimicrobial peptides (as opposed to cell-mediated immunity, or the aspect of immunity relating to phagocytes, antigen-specific cytotoxic T-lymphocytes, and cytokine response). These adjuvants provide a significant improvement over conventional materials for the induction of a humoral response. Adjuvants herein can be used with numerous vaccines, but are shown in the Examples in use with polypeptides of the invention for vaccination in dairy cows, pigs or bull calves.

Importantly, all components of adjuvants herein are of non-animal origin, thereby eliminating potential cross-contamination of vaccinated animals from potentially contaminated adjuvant components. For example, embodiments herein can utilize animal origin free Tween 80. This is particularly important when the target animal is a dairy cow, due to concerns over bovine spongiform encephalopathy (BSE) or other like bovine ailments. Note that these concerns are equally appropriate for human treatment where non-animal origin adjuvant provide significant safety benefits. Additionally, adjuvant embodiments herein are free of benzene and other like carcinogenic compounds. These embodiments provide a safety benefit not available in most conventional adjuvant compounds. For example, embodiments herein can utilize Carbopol® 974P or benzene free polycyclic acid.

In one embodiment, the immunological adjuvant comprises an oil-in-water emulsion in combination with selected antigens admixed within an emulsion premix.

Illustrative oil-in-water emulsions for use herein include combinations of mineral oil, Tween 80, Span 85 and target polymers (benzene-free Polyacrylic acid). In some cases the target polymer is selected from the group consisting of Carbomer Homopolymer Type B. Typical oil-water emulsions comprise from about 8-10% mineral oil (v/v), 0.003 to 0.004% Tween 80 (v/v), 0.007 to 0.008 Span 85 (v/v) and 0.04 to 0.06% polymer (w/v).

Illustrative emulsion premixes of the invention are composed of a high molecular weight polymer, surfactant, and emulsifier in at approximate 50% oil-aqueous base. High molecular weight polymers for use herein include acrylic acids crosslinked with allyl ethers of pentaerythritol. In some cases the high molecular weight polymers have a Brookfield RVT viscosity of between about 29,000 and 40,000, for example, Carbopol® 974P (Noveon, Inc).

Methods for Treatment of Human Disease

The invention provides pharmaceutical grade vaccines containing chimeric polypeptides and adjuvants of the invention. Such vaccines can be administered to patients having or at risk of contracting one or more diseases to cause an appropriate immunological response in a patient. Further, the methods of the invention allow vaccines to directly stimulate B cell response, improving response time and efficacy.

Vaccines of the invention are provided to patients having one or more diseases or deficiencies described herein. In one embodiment, vaccines of the invention are provided 2 to 3 times to the patient in need thereof, with little or no anamnestic response observed. In other embodiments, vaccines are provided 3 times or more, 4 or more, 5 or more, or on a continual basis. In a preferred embodiment, vaccines are readministered after a peak physiological effect or serum level is observed. In other embodiments, vaccines are readministered after the physiological effect is lessened or no longer observed, i.e. there has been a return toward or to baseline. A typical vaccine antigen amount per administration is from 1 to 5 mg/ml chimeric polypeptide. Vaccines can be administered by known techniques. In one embodiment the vaccine is administered via subcutaneous injection. In another embodiment the vaccine is administered by intradermal injection, intramuscular injection or infusion.

Vaccine embodiments of the invention can further include dispersing or wetting agents, suspension agents, or other like materials. For example, embodiments can include sterile oils, synthetic mono- or diglycerides, fatty acids or oleic acids.

Vaccines are typically prepared as sterile, aqueous solutions. These solutions are stable under conditions of manufacture and storage. In some aspects, additional agents can be included in the vaccine to prevent microorganism action, for example, antibacterial or antifungal agents.

Vaccine solutions of the invention are prepared by incorporating the materials (as described herein) in the required amounts (antigen, adjuvant, other ingredients) and can be followed by terminal sterilization, e.g., via UV light or ozone treatment. Alternatively, vaccine solutions of the invention can be prepared using individually sterilized components prior to final assembly (in which case no terminal sterilization is required).

Treatment progress for patients receiving vaccine embodiments of the invention can be monitored and additional administrations provided. Increase in deficient protein level and functional benefits (for example, a decrease in disease symptoms) are all targets for monitoring treatment effectiveness. In addition, levels of other markers can be monitored to determine effectiveness of treatment on a patient. Anamnestic response in a patient may be determined by any of the above methods or by measuring the patient's antibody titers. Based on an individual patients' progress, additional vaccine injections can be performed using more or less antigen in accordance with the present invention. In some embodiments, vaccine injections may be performed repeatedly if no anamnestic response is observed. In some embodiments, the injections are performed 3 times or more, 4 or more, or 5 or more. In other embodiments, the injections are performed continuously. In a preferred embodiment, vaccines are readministered after the peak physiological effect or serum level is observed, or alternatively after the physiological effect has returned to baseline and is no longer observed. In addition, alternative adjuvant combinations may be used to modify a particular patients' response to vaccination, as determined by the health care professional.

In some embodiments, the vaccinations are performed in an indefinite series, i.e. to treat a chronic disease or condition. Compositions of the invention are particularly useful for the long term treatment of a disease associated with a non-immunogenic protein, because the carrier composition is capable of imparting immunogenicity to a protein while not generating a significant immune response to the carrier itself. This allows the compositions to be administered repeatedly and without neutralization. Examples of chronic diseases or conditions treated by the methods described herein include growth disorders, immune disorders, cardiac disease, diabetes, stress disorders, or cancer. In some embodiments, the vaccine for the treatment of a chronic disease comprises a somatostatin-based target antigen.

Embodiments herein can be combined with other conventional therapies for the target disease state or condition. For example, somatostatin-based vaccinations of the invention can be combined with replacement insulin in the treatment of type 1 diabetes, or vaccinations can be combined with weight loss surgery or low calorie diets in a patient suffering from severe obesity. In some embodiments, vaccinations of the invention are combined with therapies that destroy or limit the effectiveness of immune cells or suppress immunological function. In a particular embodiment, vaccines of the invention are administered with therapies for autoimmune diseases (such as rheumatoid arthritis), allergies, B cell lymphomas, or carcinomas.

In some embodiments, administration of B-epitope vaccines provided herein comprising a target antigen to which an immunogenic response is desired may allow a patient with suppressed immune function to have an increased immunological response to the protein, aiding in the treatment of disease or preventing immunosuppression of a desired protein, such as an endogenous protein.

In one embodiment, the therapy is a stem cell therapy. In another embodiment, the therapy is a B cell depletion therapy that targets malignant B lineage cells. In other embodiments, the therapy is one that treats a disease state by depleting B cells or reducing B cell activation.

In some embodiments, a patient or agent of the patient identifies the best recombinant protein and linker combination based on the specific disease state and/or treatment goals. The recombinant protein is designed to allow a protein to bind to a specific linker and retain its overall conformation. In one embodiment, the recombinant protein is selected based upon a protein associated with the patient's disease state. In a particular embodiment, the recombinant protein is based upon a protein that is upregulated or amplified in the patient as compared to a healthy individual. In another embodiment, the recombinant protein is based upon a protein that is an agonist of or is upstream or downstream of a protein that is upregulated or amplified in a disease state. In yet another embodiment, the recombinant protein is based on a protein that is an antagonist of a protein that is downregulated or inhibited in a disease state. The linker is selected based on the particular structural characteristics of the carrier and recombinant protein. In some embodiments, the linker is selected for its B cell epitopes and ability to activate B cells. In other embodiments, the linker is selected for its ability to connect to the recombinant protein without causing large changes in the shape and conformity of the recombinant protein as compared to the non-recombinant or naturally occurring protein that the recombinant protein is based on.

Method for Prime-Boost Vaccination

Embodiments of the invention provide novel methods of administering a protein or antigen followed by administration of a vaccine comprising a recombinant version of the protein or antigen (i.e. a prime-boost vaccine). Proteins useful for this method include those containing B epitopes, including but not limited to influenza neuraminidase, HIV gp120, dengue fever DEN-1 and 2, hepatitis B surface antigen, *Staphylococcus aureus* surface protein (MRSA), tetanus toxin, rabies glycoprotein G, or malaria. In these embodiments, a patient is first exposed to an immunogenic amount of a protein for which an immune response is desired, for example to prevent the later development of a disease after exposure to an antigen or protein in the environment. A patient is then administered the chimeric polypeptides of the invention, which are based on a recombinant version of the protein or antigen believed to cause the disease state. Administration of vaccines comprising the recombinant protein generates antigenicity similar to that of the original protein and allows the patient to quickly develop immune responses to subsequent presentations of the protein, preventing future disease states due to subsequent exposure.

In some embodiments, vaccines comprising the modular carrier-linker of the invention may be administered as a secondary or alternative booster vaccination where another vaccine has previously been administered. In a preferred embodiment, the vaccine of the invention is based on a recombinant version of a protein used in the original vaccination. Use as a secondary or alternative booster vaccination is particularly useful where the immune system has generated immunological memory to the carriers of the original or primary vaccine. Administering the vaccines described herein prevents subsequent neutralization of the carrier, allowing efficacious additional vaccinations with an antigen. In some embodiments, the vaccine is a administered as a secondary or alternative booster vaccination where the primary vaccine is based on an antigen containing B epitopes, including but not limited to including but not limited to influenza neuraminidase, HIV gp120, dengue fever DEN-1 and 2, hepatitis B surface antigen, *Staphylococcus aureus* surface protein (MRSA), tetanus toxin, rabies glycoprotein G, or malaria.

EXAMPLES

The following examples are provided for illustrative purposes only and are not intended to limit the scope of the invention.

Example 1

CAT-Defective Somatostatin Fusion Protein

Somatostatin (also known as somatostatin-14, growth hormone inhibiting hormone, or GHIH) is a peptide hormone produced in the hypothalamus as well as certain portions of the digestive system. Somatostatin has two active forms that are produced by alternative cleavage of a polypeptide. Costoff A. Section 5, Chapter 4: Structure, Synthesis, and Secretion of Somatostatin. Endocrinology: The Endocrine Pancreas. Medical College of Georgia, page 16, incorporated by reference in its entirety for all purposes. Although it is contemplated that either somatostatin form can be used in somatostatin-based antigen embodiments herein, and that the invention includes additional antigens, somatostatin-14 will be described in detail. Somatostatin-14 is a biologically active tetradecapeptide produced in the hypothalamus and gastrointestinal tract (stomach, intestine, and pancreas). The amino acid sequence of the tetradecapeptide is AGCKNFFWKTFTSC (SEQ ID NO: 1). The sequence of somatostatin-14 is highly conserved among vertebrates (Lin X W et al. Evolution of neuroendocrine peptide systems: gonadotropin-releasing hormone and somatostatin. Comp. Biochem. Physiol. C. Pharmacol. Toxicol. Endocrinol. 1998 119(3):375-88.) The tetradecapeptide is encoded by a nucleic acid sequence: GCTGGCTGCAAGAATTTCTTCTGGAAGACTTTCACATCCTGT (SEQ ID NO: 15) (note that other nucleic acid sequences can be used to code SEQ ID NO: 1, however, SEQ ID NO: 15 is provided for illustrative purposes).

Somatostatin-14 is known to have a strong inhibitory effect on a large number of hormones involved in the growth and utilization of food in animals, especially growth hormone and insulin. As previously described in U.S. Pat. Nos. 6,316,004, 7,722,881 and U.S. Patent Publication No. 2013/0149332 (incorporated herein by reference for all uses), somatostatin-14 and chimeric versions of somatostatin can be used in immunization of animals for increase in daily weight and, where appropriate, milk production. Unlike the current invention, these immunization procedures did not provide multiple administrations without anamnestic responses. Note that treatment of target animals with anti-somatostatin antibodies has proven to be overly costly and functionally non-dramatic, thereby eliminating direct antibody treatment as non-practical. Muromtsev G. S., et al., 1990, Basics of agricultural biotechnology, Agropromizdat, Moscow, pp 102-106. One aspect of the present invention is based on the concept that the anti-somatostatin antibodies formed by compositions and methods described herein attenuate but do not completely eliminate the mostly inhibitory actions of somatostatin in the target animal. This process produces a natural and proportional increase in growth and productivity in immunized target animals.

In particular, immunization of animals to somatostatin has been recognized as a means of neutralizing somatostatin in a target animal and thereby removing somatostatin's normal inhibitory effects on various aspects of the animal's productivity, e.g. milk production in a dairy cow (Reichlin S., ed., Somatostatin, Basic and Clinical Status. Plenum Press, New York 1987, pp 3-50, 121-36, 146-56, 169-82, 221-8, 267-74; Spencer, G. S., Review: Hormonal systems regulating growth. Livestock Production Science 1985; 12:31-46. Importantly, these somatostatin-based immunization procedures avoid the direct use of anabolic hormones, e.g. growth hormone and the like, in the animal, and allow for small changes in the concentration of the endogenous anabolic factors and thereby provide ecologically pure food products.

A number of studies have shown that animals immunized with somatostatin have an average daily gain of 10-20%, an appetite reduced by 9% and an 11% increase in the efficiency of food utilization. Animals immunized with somatostatin, and also their offspring, have correct proportions, and the distribution of the weight of the animals between the muscles, bones and fat is the same as in control animals (see Reichlin, 1987). Therefore, somatostatin immunization provides a useful and safe way of enhancing a target animal's productivity. This is particularly the case when compared with use of recombinant growth hormone, which use has raised concerns over hormone in milk or meat from treated animals or for the safety of the animals themselves or for build-up of the hormone in the ecosystem, particularly the ground water supply.

Somatostatin is known to have a relatively short half-life in the blood. In order to enhance the immunologic effects of somatostatin, immunization protocols have been developed to enhance the protein's half-life by conjugating somatostatin to target carrier proteins. These conjugated somatostatin proteins are designed to have increased half-life and increased antigenicity in the blood and therefore provide enhanced benefits, especially in light of the cost of preparing somatostatin. For example, chimeric somatostatin proteins are disclosed in U.S. Pat. No. 6,316,004, corresponding European Patent EP0645454, and U.S. Pat. No. 7,722,881, each of which is incorporated herein by reference, where various conjugated somatostatin-containing proteins are shown to have increased antigenicity and function with regard to productivity of farm animals as compared to other conventional immunization or anabolic hormone-based procedures. U.S. Patent Publication No. 2013/0149332 discloses similar compositions and shows their beneficial use in other diseases, including human obesity.

These methods provide an unexpected improvement over other methods of administering vaccines.

The present example illustrates the production of a CAT-defective somatostatin fusion protein in accordance with embodiments of the present invention. Site-directed mutagenesis was performed on plasmid pET30b-Cat-Som to replace His192 and His193 with glycine residues (after modification: Gly192 and Gly193). Inactivation of the His193 (and His192) residues eliminates the capacity of the CAT enzyme to accept protons, thereby providing complete inactivation of the CAT.

The linker in the same pET30b-Cat-Som (having the His replacement(s)) was codon-optimized for expression by E. coli in the absence of co-expressed tRNA molecules.

The modified CAT-defective somatostatin nucleic acid construct is shown as SEQ ID NO: 12. The CAT-defective somatostatin fusion protein sequence is disclosed as SEQ ID NO: 13, being compared to an unmodified CAT-somatostatin fusion protein (SEQ ID NO: 14).

Example 2

CAT-Defective Somatostatin Fusion Protein can be Expressed at High Levels

The codon-optimized CAT-defective somatostatin construct as described in Example 1 was used to express the fusion protein in BL21(DE3) cells. Transformed cells were grown in LB and induced with 0.4 mM IPTG for approximately three hours. One milliliter of cells from a density of OD 0.7 culture were pelleted, and heated at 70° C. for ten minutes in 100 µl SDS sample buffer. A sample of 40 µl of cell extract was loaded per lane for SDS PAGE.

28 KD band corresponding to the predicted size of a codon-optimized, CAT-defective somatostatin fusion protein was visible in lanes 1 (LB+IPTG, reduced) and 3 (LB+IPTG) after induction with IPTG. No expression is seen in control lanes 2 (LB, reduced) and 4 (LB). As expected, there was no difference in fusion protein size when run under standard or reducing conditions.

Example 3

Endotoxin Free, Codon-Optimized CAT-Deficient Somatostatin Containing Vaccine

An illustrative vaccine comprising the fusion protein of the previous examples in accordance with the present invention:

Reagent Solution:
1. Carbopol Base
   a. Dissolve 0.5 grams of Carbopol 974P in water or saline
   b. Mix and boil to dissolve. Followed by autoclaving.
   c. Store at 4° C.

2. Squalene Base
   a. Mix 58.1 ml of squalene, 4.6 ml of non-animal origin Tween 80 and 5.2 ml of Span 85.
   b. Mixture was filtered through a 0.2μ filter.
   c. Store at 4° C.
3. Tragacanthin solution
   a. Extract tragacanth gum with methanol.
   b. Collect methanol insoluble fraction.
   c. Dry at room temperature.
   d. Store at room temperature in a desiccated state,
   e. Add 1 gram of dried Tragacanthin in water or saline.
   f. Mix and boil to dissolve, followed by autoclaving.
   g. Store at 4° C.

Vaccine Preparation
1. Vaccine antigens are prepared in saline or PBS at 5 mg/ml or lower.
2. Add 6.79 ml of squalene base to mixing bottle.
3. Add 10 ml of Carbopol base to Squalene base. (CS)
4. Mix well.
5. Add 10 ml of Tragacanthin solution to CS solution.
6. Mix well.
7. Vaccine antigens, undiluted or diluted to use in saline or PBS, are added to a final volume of 82 ml.
8. 1 ml of a 1% Thimerosal solution is added and mixed well.
9. Store vaccine at 4° C. until use.

Alternative illustrative vaccine in accordance with the present invention:
Reagent Solutions:
1. Carbopol Base:
   a. Dissolve 0.5 grams of Carbopol 974P in water or saline;
   a. Mix and boil to dissolve; and autoclave
   b. Store at 4° C.
2. Squalene Base:
   a. Mix 58.1 ml of squalene, 4.6 ml of non-animal origin Tween 80 and 5.2 ml of Span 85; and filter through 0.2μ filter
   b. Store at 4° C.
3. Arabinogalactan solution:
   a. Add 1-10 grams of arabinogalactan into PBS or saline;
   b. Mix and boil to dissolve; and autoclave
   c. Store at 4° C.

Vaccine Preparation:
1. Vaccine antigens are prepared in saline or PBS at 5 mg/ml or lower;
2. Add 6.79 ml of squalene base to mixing bottle;
3. Add 10 ml of Carbopol base to the Squalene base;
4. Mix thoroughly and add 10 ml of arabinogalactan solution;
5. Antigens of the invention, undiluted or diluted, to use in saline or PBS, are added to a final volume of 82 ml.
6. 1 ml of a 1% thimerosal solution is added and the vaccine mixed; and
7. The vaccine is stored at 4° C. until use.

Example 4

Treatment of Cardio Vascular Disease Using Vaccine of Example 3

The present Example uses rats with left ventricle dysfunction as prepared in the protocol published in Genentech, 1995. Two groups of rats are segregated (each member of each group having a ligated left coronary artery), a first treatment group receives the vaccinations of the invention and a second control group (no vaccination, but otherwise treated the same). Each member of the treatment group receives a vaccination and then 21 days later a second vaccination and a third vaccination at 42 days, administered intramuscularly (1 ml/dose). Serum IGF-1 levels and anti-somatostatin antibodies are measured at day 0, day 21, day 42 and day 63. At day 63, hemodynamic parameters are also measured in both groups as well as a determination of infarct size and cardiac index.

It is anticipated that the rat group receiving the three vaccinations, as described in Example 3, would have substantially improved cardiac function (decrease infarct size and improved cardiac index) as compared to the control group. It is also anticipated that rat groups in further studies, in which the vaccinations are repeated at regular intervals over a substantial or indefinite period of time, would continue to have substantially improved cardiac function as compared to the control group. This makes vaccines of the invention particularly useful in the long-term treatment of cardiovascular disease.

Example 5

Treatment of Growth Deficiency Using Vaccine of Example 3

Three week old Cox (CD) rats will be vaccinated monthly for 3 months using a 1 ml dose. Each vaccination will occur intramuscularly or subcutaneously. Control rats will receive saline injections, using the same mode of administration and the same volume of material for administration. All rats will be weighed to determine growth on a weekly basis and bled at 0, 4, 8, 12 and 16 weeks. Serum will be collected at a similar schedule and analyzed for IGF-1, urea and anti-somatostatin antibody levels.

It is expected that CD rats receiving vaccinations as described in Example 3 will have substantially improved growth as compared to control CD rats. Treated rats should show serum results that confirm vaccinations effects on treated rats. It is also anticipated that rat groups in further studies, in which the vaccinations are repeated at regular intervals over a substantial or indefinite period of time, would continue to have substantially improved cardiac function as compared to the control group. This makes vaccines of the invention particularly useful in the long-term treatment of growth deficiency.

Example 6

Treatment of Obesity in Mice

Mouse obesity studies were performed using mice from Jackson Laboratories, Bar Harbor, Me. A number of inbred mice from line C57BL/6J were obtained from Jackson Laboratories, the mice were: male, showed induced severe obesity, had polygenic genetics, and exhibited mature onset obesity. In previous testing, Jackson Laboratories had determined that this particular strain of mice, when fed on a high fat diet, develops metabolic syndrome phenotypes very similar in nature to those reported in the human population. For example, C57BL/6J mice fed a high fat diet will show visceral adiposity, insulin resistance, hyperinsulinemia, hyperleptinemia, leptin resistance and hypertension.

Studies were conducted to test the effectiveness of vaccine embodiments herein for treating obesity, i.e., including limiting weight gain in some mice to causing weight loss in C57BL/6J mice. Six week old mice were fed a 60% kcal % fat diet for 6 weeks. Twelve week old mice were then broken into one of four groups: group 1 included mice treated with JH14 containing vaccine; group 2 included mice treated with JH17 containing vaccine, group 3 included mice treated with JH18 containing vaccine, and group 4 included control mice that were treated with PBS rather than any type of anti-somatostatin type antigen. Mice in each group were vaccinated using a 0.5 ml of the specified vaccine or PBS via an IP route. After twenty two days the mice were treated again with a second IP dose using 0.1 ml of vaccine.

Throughout the course of the study (6 weeks) each mouse was weighed two times per week and food intake monitored, i.e., to ensure that weight changes were not due to loss or increase in food intake. A terminal bleed was performed on each mouse at the conclusion of the study and IGF-1 levels determined (IGF-1 plasma levels were determined using Diagnostic Systems Laboratories Inc. Active Mouse/Rat IGF-1 ELISA (DSL-10-29200).

As shown in Table 3, mice treated with JH14, 17 and 18 all showed a highly significant difference (p<0.0001) by parametric or non-parametric statistical analyses) in percent Final Body Weight vs. Baseline Weight. Significant weight loss was observed in each vaccinated group within the first 7 days while the control group showed slight weight gain over the same time period. A small weight loss was also observed after the second dose of vaccine (⅕ dose provided on day 1) was administered to the JH14, JH17 and JH18 groups at day 22.

Data from the mouse obesity study provided the following conclusions: (1) although there is not a statistically significant difference between JH18 and the controls, in terms of IGF-1 ng/ml, there is a highly significant difference between these groups (P<0.0001) by parametric or non-parametric statistical analysis in percent Final Body Weight versus Baseline Weight; (2) In percent Final Body Weight versus Baseline Weight, JH17 versus the controls produced a statistically significant difference by both statistical tests; (3) JH18 (which had a mean IGF-1 level of 135.8 ng/ml more than JH17), demonstrated a statistically significant difference versus JH17 in percent baseline weight (only by the non-parametric test); (4) chimeric-somatostatin antigen of the invention in both JH17 and JH18 adjuvants induced a statistically significant difference in percent Final Body Weight versus Baseline Weight; (5) JH18 was statistically significant when compared with JH17 by non-parametric analysis in terms of percent Final Body Weigh versus Baseline Weight; (6) IGF-1 levels can be correlated with a greater weight loss at the end of the study versus both controls and JH17 vaccinates (see Table 4); (7) since all vaccinates had the same dose amounts of the chimeric-somatostatin antigen of the invention, an adjuvant affect was observed within the study; (8) inbred C57BL/6J male mice fed 60% kcal fat diet demonstrated a significant weight loss within the first week post IP vaccination; and (9) the weight loss shown herein persisted even while the mice ate a 60 kcal % fat diet for the duration of the study.

TABLE 3

Final Body Weight versus Baseline Weight

| Group | # | % Baseline | Standard Deviation | Mann Whitney (two tailed) | Unpaired t-test (two-tailed) |
|---|---|---|---|---|---|
| Controls | 10 | 115.5 | 6.3 | Not Done | Not Done |
| JH17 | 10 | 107.1 | 4.7 | P = 0.0021 | P = 0.033 |
| JH18 | 10 | 104 | 3.0 | P < 0.0001 | P < 0.0001 |
| JH17 vs. JH18 | — | — | — | P = 0.0355 | P = 0.1016 |

TABLE 4

IGF-1 Statistical Analysis

| Group | # | Mean IGF-1 (ng/ml) | Standard Deviation | Mann Whitney (1 tailed) |
|---|---|---|---|---|
| Controls | 10 | 365.6 | 88.7 | Not Done |
| JH17 | 10 | 304.2 | 99.2 | P = 0.0827 |
| JH18 | 10 | 440.4 | 103.7 | P = 0.105 |

Example 7

Endotoxin Free Chimeric Peptides/Adjuvants Provide Increased Milk Production

A random pool of dairy cows (Holstein Crosses—US bred and raised) was identified, each was 31 to 65 days post-calving ($3^{rd}$ through $5^{th}$ lactation). Each cow was examined and determined to be in optimal health by a veterinarian.

The average cow weight in the study was from about 1,000 to 1,200 lbs. Six lactating cows were treated with 1.96 mg/chimeric protein/2 ml dose in JH14. Alternatively, 9 lactating cows were provided with a conventional rB ST treatment. Treatments and milk production study was conducted at a large scale, intense milk production dairy.

Vaccinations were conducted at day 0. Anti-SST serum antibodies and IGF-1 serum levels tested at 4 weeks. Milk production and identification of general health of animals were conducted on a regular schedule.

Six cows that were vaccinated using inventive compositions described herein had a normal appearance, with no endotoxin reaction or food withdrawal. All six cows had a positive serologic response to SST with a mean titer of 1:14. Milk production of the six cows was obtained with only one vaccination, showing a mean yield increase of 23.7%.

Nine cows treated using conventional rBST injections at 0 and 14 days with an overall mean increase in milk productivity of 2%.

The data in this Example shows the drastic improvement in effectiveness for using the endotoxin free constructs in combination with inventive adjuvants in dairy cows. These results are dramatically improved toward the animal's health and productiveness as compared to cows rejected two times with rB ST.

Example 8

Multiple Vaccinations with Chimeric Peptides/Adjuvants Increase Milk Production

A pool of 92 clinically healthy dairy cows (Primiparous and Multiparous Girilander and Girilander/Holstein crosses) was identified, each was 90 to 120 days post-calving. The cows were divided into four treatment groups, with one receiving a single vaccine dose, one receiving a double dose, one receiving a quadruple dose, and a saline control group.

Treatments and milk production study was conducted at a large scale, intense milk production dairy.

Cows were vaccinated intramuscularly in the neck region on days 0, 21 and 42 of the study, with the injection site alternating from right to left to right. The cows were milked 3 times a day according to the farm's practices, and milk yields were recorded for each cow. Milk was analyzed for milk fat, lactose, protein, urea and Somatic Cell Count (SCC). Cows were observed daily for injection site reactions, general health, mastitis and foot problems, and body scores were obtained at 21 day intervals. The study concluded 21 days post $3^{rd}$ vaccination, or 63 days from its start.

Figure 3:
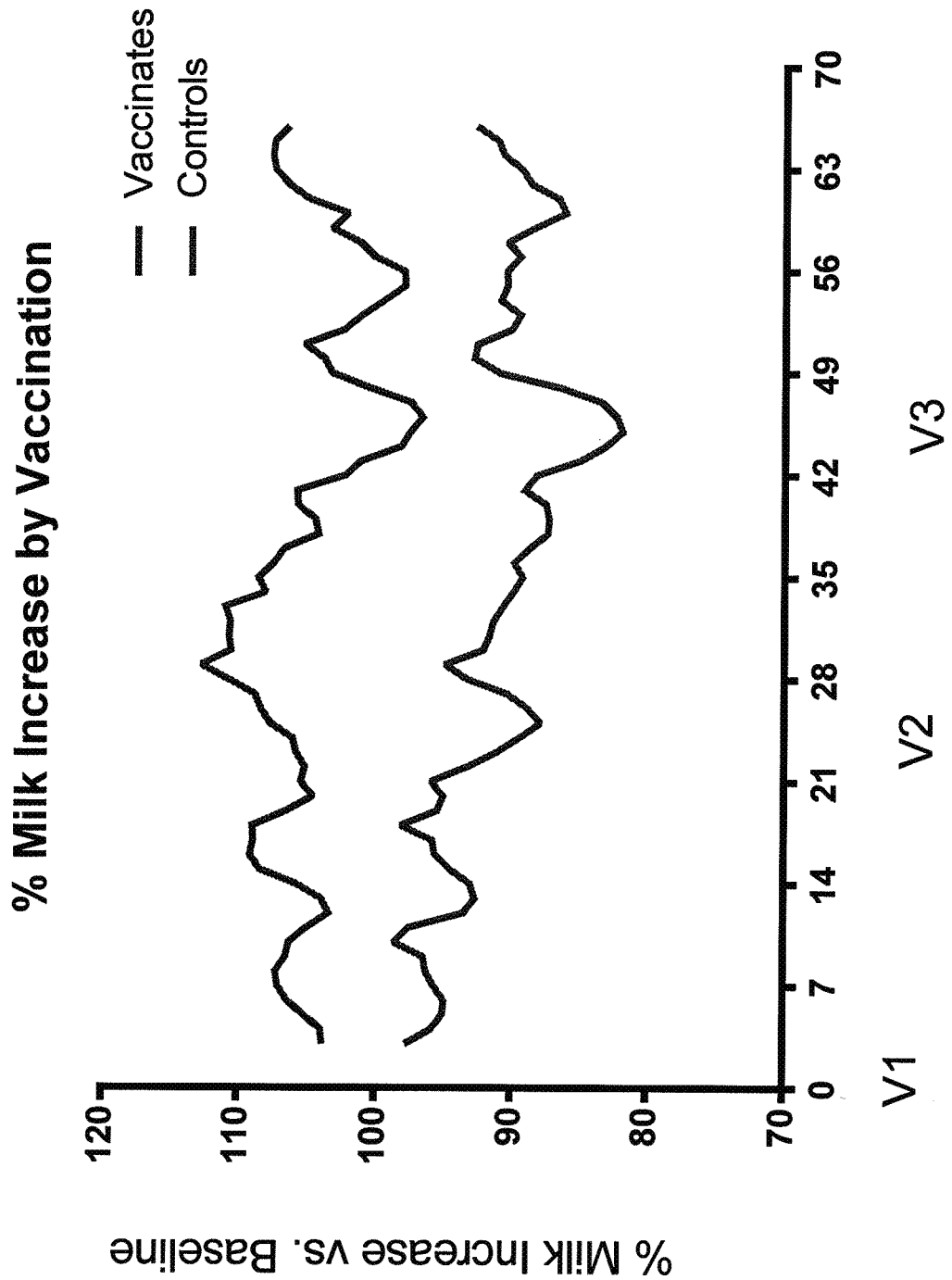
FIG. 3 is a graph showing the milk increase of vaccinated cows by each vaccination as compared to control cows in accordance with aspects of the present inv -continued

The treated cows showed increased milk yields compared to pre-vaccination yields, with increases beginning by day 4 post-vaccination and persisting through day 21, with peak yields 8-14 days post vaccination. As shown in FIGS. 3 and 4, this trend was repeated upon each of the three vaccinations. As compared with control cows, vaccinated cows demonstrated an increase of 5-20% in milk production in the post vaccination periods, with a mean increase in milk yield of 13.6%. Using an LSmeans model, there was a highly statistical difference in milk production between treatment weeks.

No significant differences were observed among the treatment groups with respect to site reactions, body scores, general health, mastitis or foot problems. Vaccination, even at a quadruple dose, was well tolerated by the cows and produced no untoward effects as compared to the controls.

The data in this Example shows the surprising finding that multiple repeated injections of the compounds of the invention are highly efficacious for rapidly increasing milk production, and that the increased production may be sustained using multiple injections over a lengthy period. It would be expected that multiple or repeat injections at regular intervals over a substantial or indefinite period of time would continue to cause improved milk production. This makes vaccines of the invention particularly useful in the long-term improvement of milk production.

Example 9

Endotoxin Free Chimeric Peptides/Adjuvants Provide Increased Meat Production in Piglets of Treated Sows A random pool of sows will be identified, each being at least 35-36 days prior to farrowing. Each sow will be examined and determined to be in optimal health by a veterinarian. Pregnant sows will be immunized two times using vaccines of the invention (see Example 3), once at 35-36 days prior to delivery, and once at 8 days prior to delivery. A control group of pregnant sows will be maintained for comparison purposes (no vaccinations or vaccination with sterile saline).

Delivered piglets from the vaccinated group will have greater survivability and be of a greater average size. It is the increase in piglet size that enhances the percent survivability, as larger piglets are less likely to be pushed away from the sow's teat. Treated and control piglets will be weighed at day 21, day 30 and day 75. Vaccinations of the present invention will increase the piglet daily weight by an average of 35% over the course of the 75 day period.

Importantly, piglet survivability and weight are increased through use of the vaccines of the present invention in the absence of recombinant growth hormone. This is a significant improvement over recombinant hormone therapy.

Example 10

Endotoxin Free Chimeric Peptides/Adjuvants Provide Increased Meat Production in Treated Pigs 36 barrows of pigs were purchased from a commercial source as feeder pigs, each weighing approximately 22 kg. After a one week acclimation period, the pigs were fasted overnight and then weighed to establish weight blocks. Pigs from each of the weight blocks were allotted at random to three treatment groups as follows: saline control (control group), JH14 adjuvant containing 0.1 mg/ml of recombinant Human Serum Albumin (rHSA) adjuvant (adjuvant group), and JH14 adjuvant containing 0.5 mg/ml of SST-CAT chimeric protein (vaccine group). The pigs were housed in individual pens (n=12) and provided feed and water ad libitum. A common corn-soybean meal-based diet was fed to both treatment groups and formulated to ensure that inadequate nutrient supply does not impair animal response to treatment.

Initial blood samples for serum recovery were obtained by jugular venipuncture. All vaccinations were with 1 ml administered intramuscularly. Subsequent vaccinations were administered at 4 and 8 weeks, and blood samples were collected bi-weekly for serum recovery, serum hormone and metabolite measurement, and to measure antibody titers. Serum metabolites (NEFA, triglycerides, glucose and urea nitrogen) were measured in an auto-analyzer in a clinical pathology laboratory, while porcine insulin, IGF-1 and somatostatin were measured by commercially available ELISA kits. Serological responses were monitored by ELISA utilizing rCAT, sSST and rHSA as coating antigens. Body weight and feed intake data were also collected bi-weekly to determine average daily gain. At the conclusion 12 weeks after initial vaccination, final body weight and feed intake measures were taken after an overnight fast, and final blood samples were obtained. Thereafter, pigs were allowed to consume feed ad libitum until three hours prior to euthanasia on the following day, followed by processing in a certified processing facility.

TABLE 5

| Differential weight gain (Δ gain) by VAX group pigs compared to control. | | |
|---|---|---|
| Time Period | Weeks Post $3^{rd}$ Vaccination | Mean Δ gain (kg) |
| Week 8 | 0 | 0 |
| Week 9 | 1 | 2.3 |
| Week 10 | 2 | 2.34 |
| Week 11 | 3 | 2.97 |
| Week 12 | 4 | 3.3 |

Figure 5A:
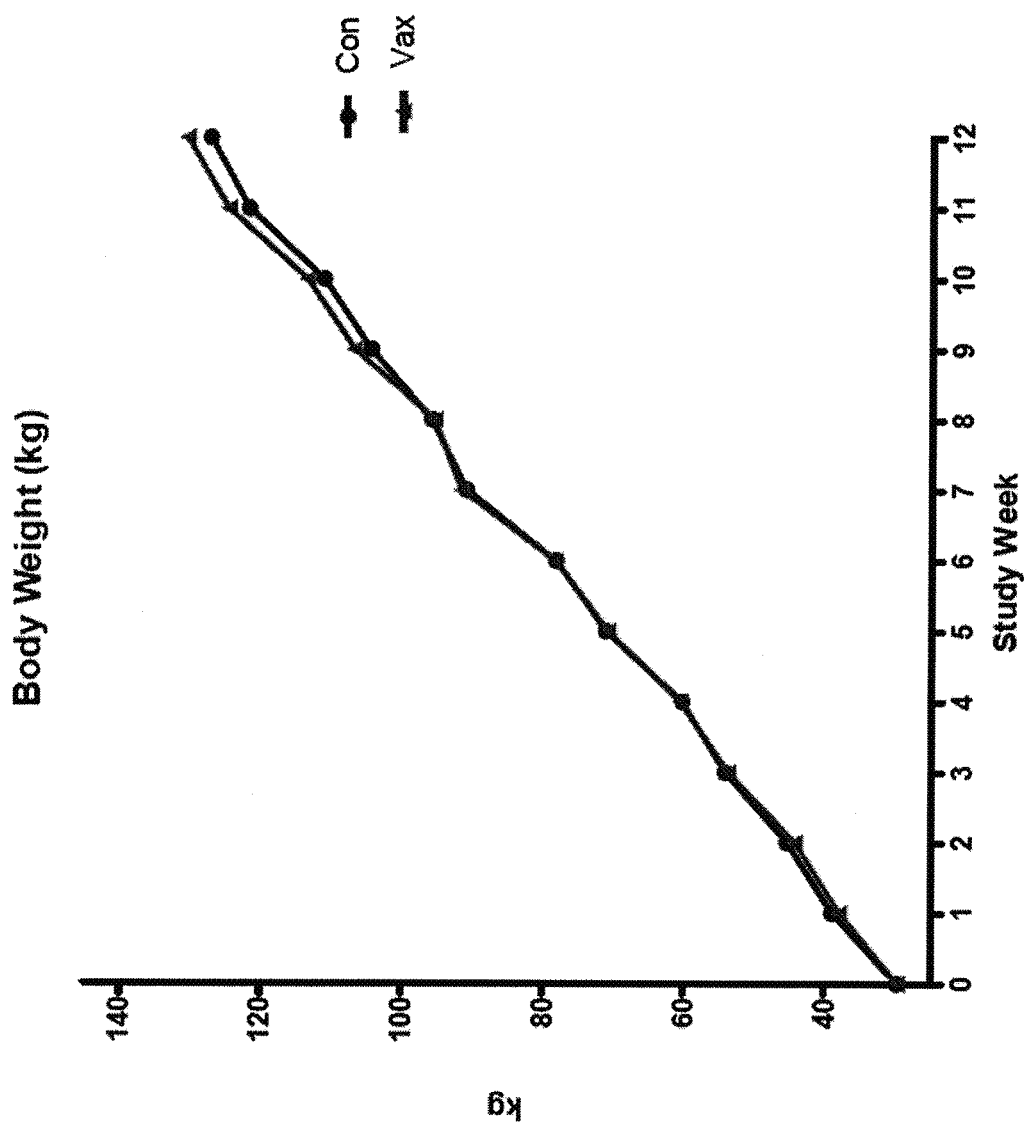
Figure 5B:
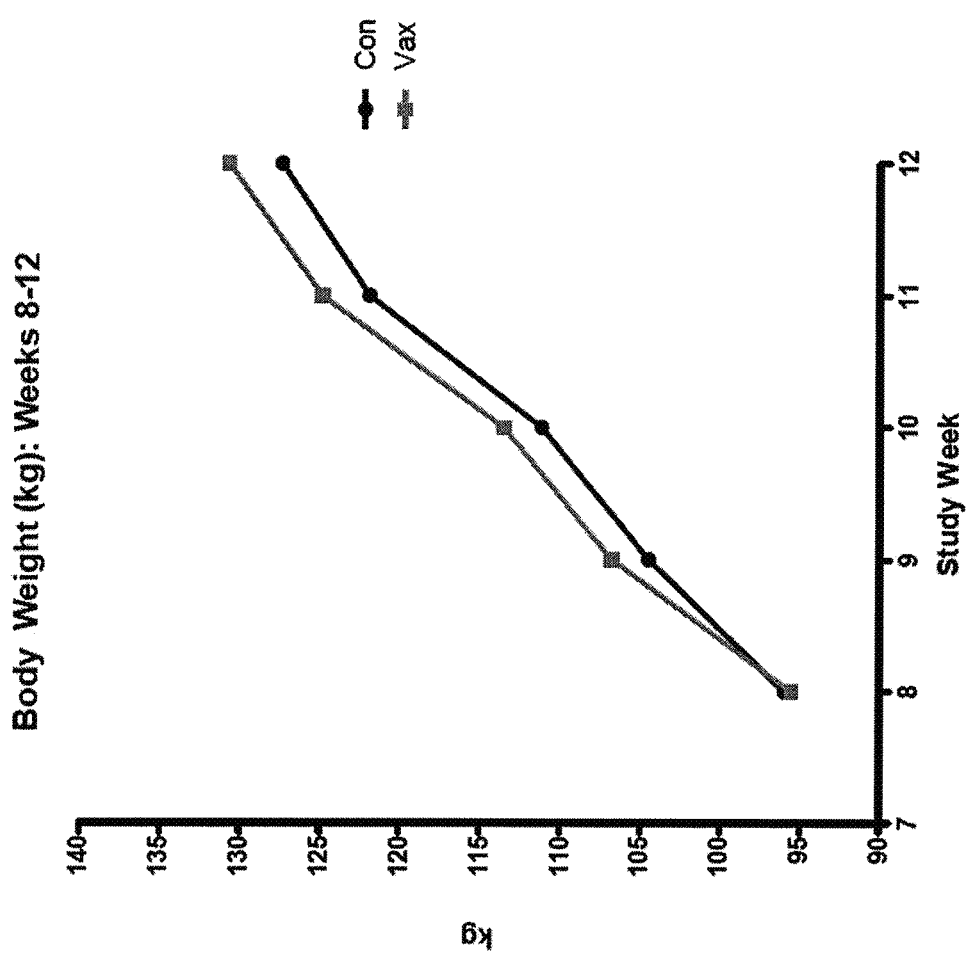
Figure 5C:
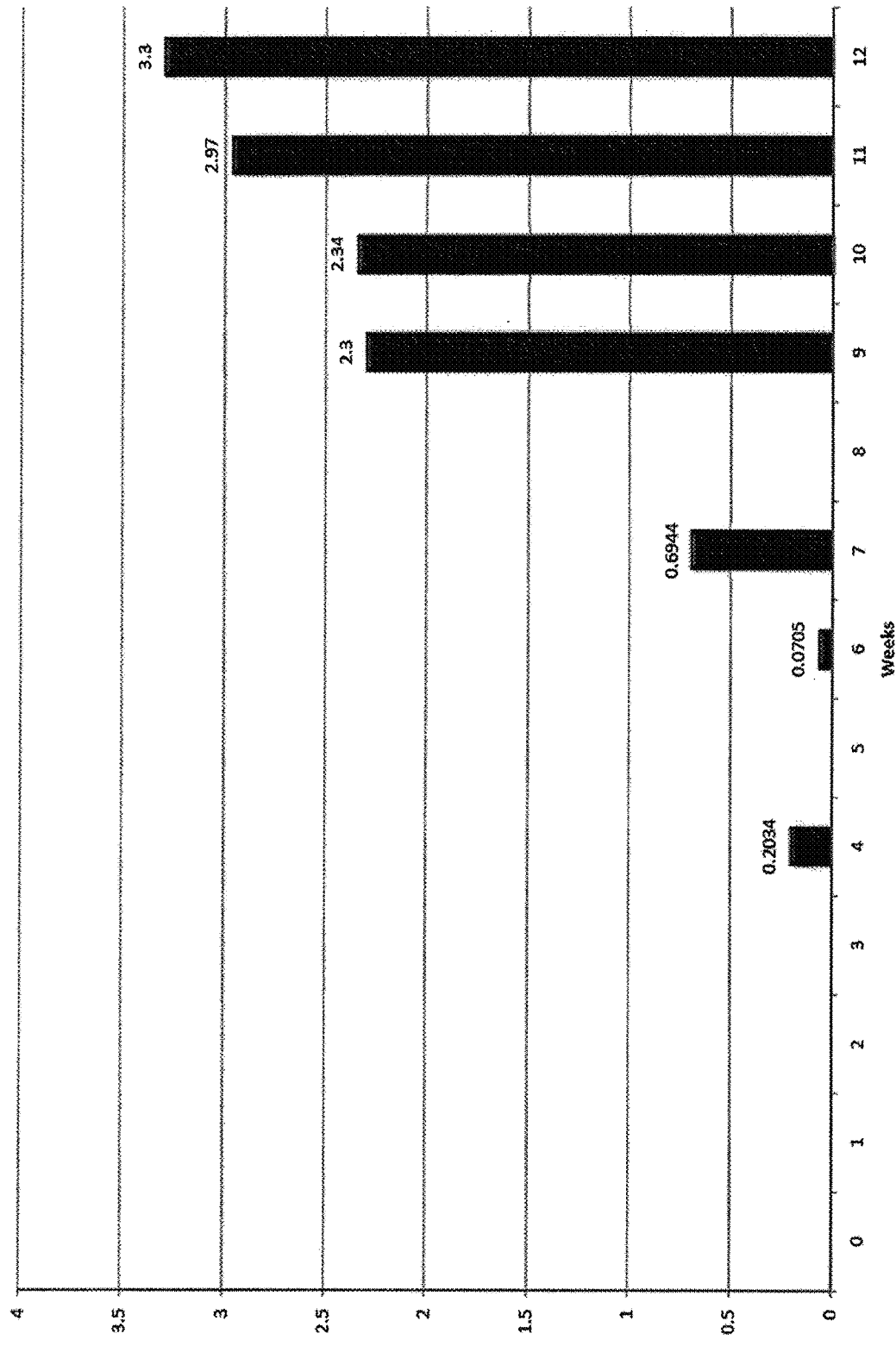

As compared to controls, vaccination group pigs demonstrated an increase in weight gain post $3^{rd}$ vaccination. Overall, three was a significant increase in body weight over the 12 week study, as shown in Table 5 and FIG. 5A. The increase was particularly large in the final four weeks (FIG. 5B). FIG. 5C shows the difference in mean body weight between vaccinated and control pigs.

The cumulative weight differences for the entire 12 week study period were 3.4 kg, as shown in FIG. 5C.

Figure 6:
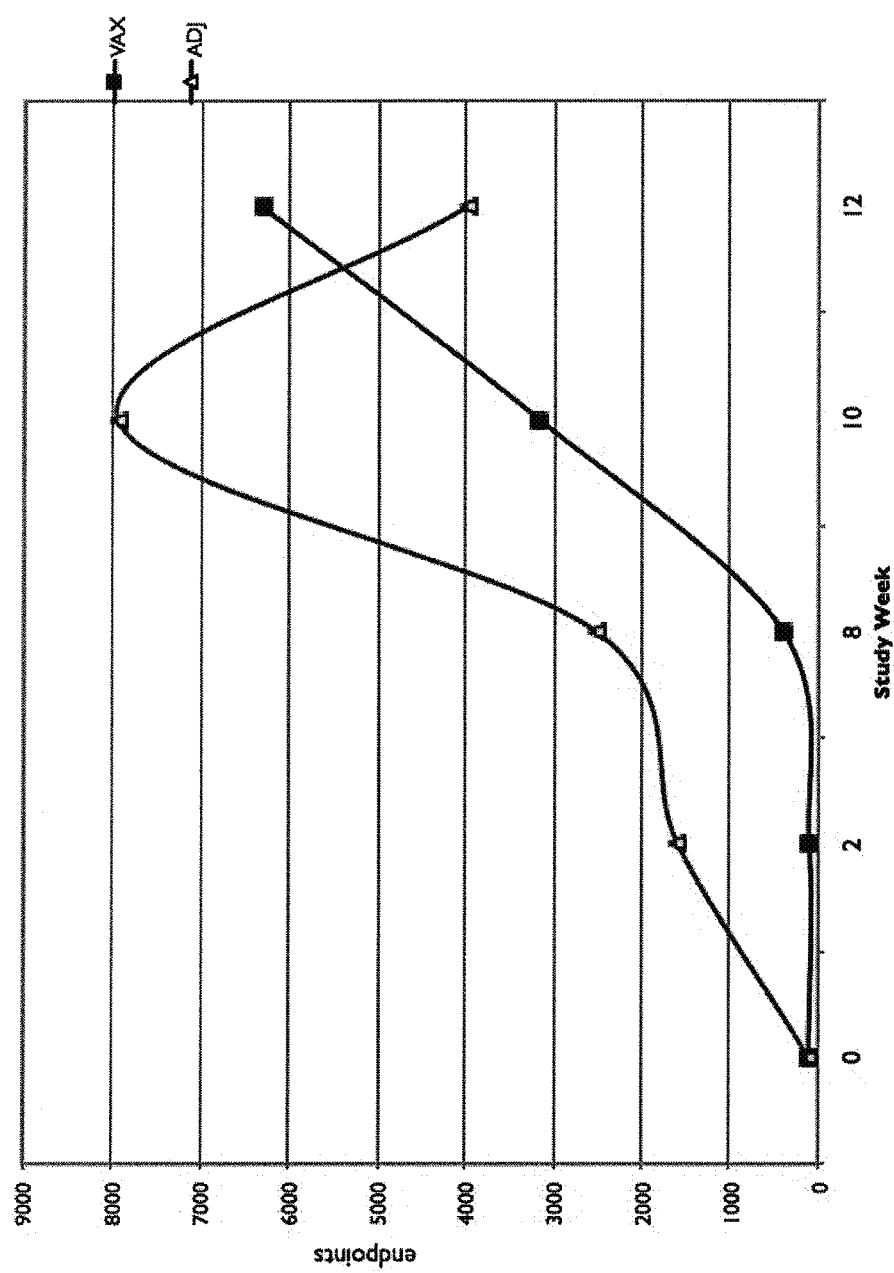

As shown FIG. 6, ELISA responses to the indicator control antigen (rHSA) were similar to the responses to rCAT, indicating normal immune function in the vaccination group. However, responses to CAT did not demonstrate enhancement until after the 3$^{rd}$ vaccination (week 8), and unlike rHSA did not demonstrate a titer drop (plateau effect) post 10 weeks. Of the 12 pigs in the vaccination group, positive serological responses were observed in 100% of the pigs from week 8 through week 12. The responses to CAT were similar to Human Serum Albumin (HSA) vaccines, but the somatostatin responses were somewhat different.

Figure 7:
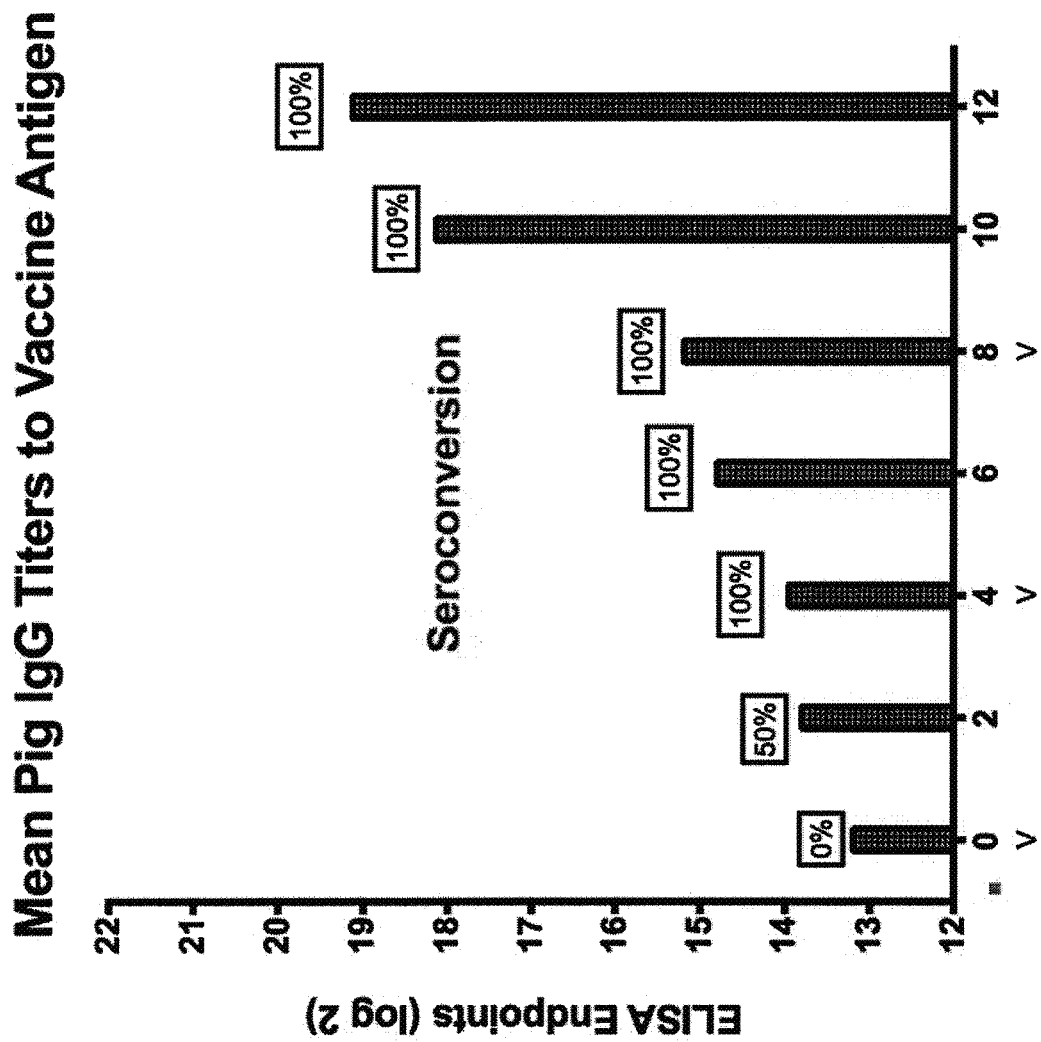
Figure 8:
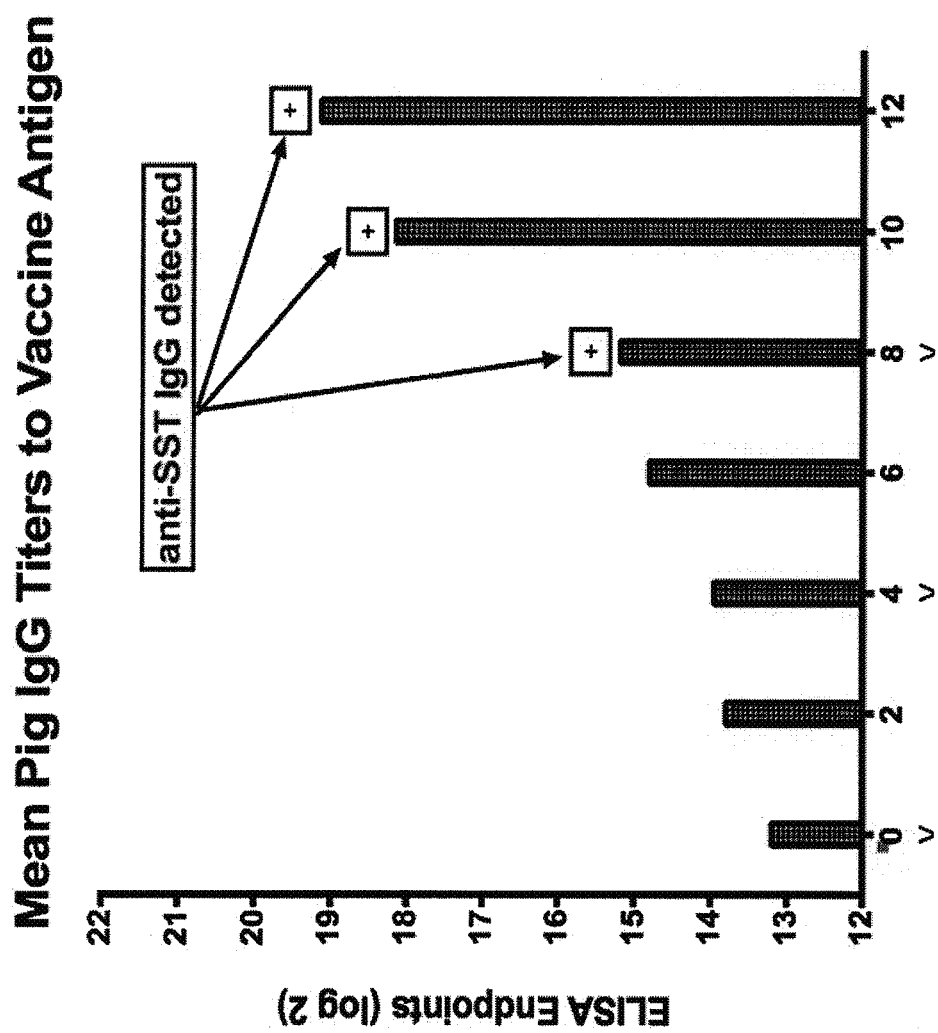

In the same period, serological responses to rSST are shown in FIGS. 7 and 8. Surprisingly, 100% seroconversion was seen from week 4 to week 12, as shown in FIG. 7. Significant increases in anti-SST IgG were detected at weeks 8, 10 and 12, as shown in FIG. 8.

The study results did not indicate any deleterious side effects due to vaccination, and injection site observation at processing did not indicate any macroscopic pathology or meat quality issues. Serum metabolite and hormone levels, determined at 12 weeks and shown in Table 7 indicated no statistically significant changes in the vaccinated group as compared to control pigs.

TABLE 6

Summary of weight gain in piglets

|  | CONTROLS (n = 10) | VACCINATES (n = 10) |
| --- | --- | --- |
| Final Weight (kg) | 127.5 | 130.7 |
| Gain from week 0 (kg) | 97.6 | 101.03 |
| Body Mass index | 58.4 | 60.4 |

TABLE 7

Pig measurements at 12 weeks of the study (4 weeks post 3$^{rd}$ Vaccination)

| Hormone/Metabolite | Controls | Vaccinates |
| --- | --- | --- |
| Somatostatin (pg/ml) | 24.9 | 27.3 |
| Serum Triglycerides (mM) | 1.8 | 2.4 |
| Serum IGF-1 (ng/ml) | 23.6 | 22.2 |
| NEFA (mM) | 0.39 | 0.40 |
| Glucose (mg/dL) | 103.39 | 113.35 |
| Serum Urea (mg/dL) | 60.5 | 54.3 |
| Insulin (ng/ml) | 0.247 | 0.384 |

The data in this Example shows that multiple repeated injections of the compounds of the invention are highly efficacious for improving meat production, and that the increased production may be sustained using multiple injections over a lengthy period. The lack of an observed boosting effect due to endogenous somatostatin results in an improved ability to repeatedly vaccinate the animals, resulting in improved product yields.

Example 11

Endotoxin Free Chimeric Peptide/Adjuvants Provide Increased Meat Production in Treated Bull Calves A random pool of bull calves, one to three months of age, will be identified, and injected with compositions of the invention. Weight increase over a period of approximately ten months will be monitored and compared to a control group, the control group being treated the same in every sense as the injected group except for the vaccine injections of the invention. Each bull calve will be examined and determined to be in optimal health by a veterinarian over the course of the treatments.

Injections herein for the vaccinated group are performed at zero weeks, 4 weeks and 8 (three total vaccinations). Vaccinations will be provided subcutaneously or intramuscularly to the neck using 18-21 gauge cc needle. Booster injections were also provided (4 boosts, three boosts or no boosts). Vaccination injections included 2 mg/2 ml of the chimeric polypeptide. The chimeric polypeptide was prepared as described herein having both histidine residues in CAT replaced with glycine amino acids of the invention and an optimized linker as described by SEQ ID NO: 4.

Vaccinated bull calves and control calves are each weighed to take an initial weight. It is expected that vaccinated animals herein will show a 15 to 40% weight increase over control animals. This increase in average weight for treated bull calves shows a significant advantage over no treatment.

Importantly, harvested meat from treated bull calves does not contain recombinant growth hormone.

Example 12

B Cell Epitope Prediction for Polypeptide Conjugates

The BepiPred 1.0 method was used as described by Larsen, Ole Lund and Morten Nielsen, "Improved method for predicting linear B-cell epitopes", Immunome Research 2:2, 2006, which is incorporated herein by reference, and as found in http://www.cbs.dtu.dk/services/BepiPred/, to predict B-cell epitopes in a polypeptide conjugate and component target antigen, carrier polypeptide, and linker polypeptides. Model predictions were initially based on amino acid sequences disclosed in Chloramphenicol Acetyl Transferase (CAT)-Defective Somatostatin Fusion Protein disclosed in U.S. Pat. Nos. 7,722,881 and 8,425,914, each of which is herein incorporated herein by reference. The following sequences were used in the calculations.

Model target antigen: somatostatin 14: SST:
(SEQ ID NO: 1)
AGCKNFFWKTFTSC (14 Aas)

Model linker polypeptide:
(SEQ ID NO: 10)
welhrsgprprprprpefm (19 Aas)

Model carrier polypeptide: inactivated CAT enzyme (corresponding to his→gly at both 192 and 193):
(SEQ ID NO: 3)
Mekkitgyttvdisqwhrkehfeafqsvaqctynqtvqlditaflktvkk nkhkfypafihilarlmnahpefrmamkdgelviwdsvhpcytvfheqte tfsslwseyhddfrqflhiysqdvacygenlayfpkgfienmffvsanpw vsftsfdlnvanmdnffapvftmgkyytqgdkvlmplaiqv*gg*avcdgfh vgrmlnelqq (210 Aas)

Model linker-SST:
(SEQ ID NO: 30)
welhrsgprprprprpefmAGCKNFFWKTFTSC (33 Aas)

-continued

Model polypeptide conjugate: carrier-linker-SST:
SEQ ID NO: 13

(SEQ ID NO: 13)
mekkitgyttvdisqwhrkehfeafqsvaqctynqtvqlditaflktvkk nkhkfypafihilarlmnahpefrmamkdgelviwdsvhpcytvfheqte tfsslwseyhddfrqflhiysqdvacygenlayfpkgfienmffvsanpw vsftsfdlnvanmdnffapvftmgkyytqgdkvlmplaiqvggavcdgfh vgrmlnelqqwelhrsgprprprprpefmagcknffwktftsc (243

Aas)

Employing these sequences, predicted B-cell epitopes were calculated using the Bepipred 1.0 method. Results are shown in Table 8.

TABLE 8

B-cell epitope scores for Polypeptide Conjugate.

| Protein | # AA | # > 0.2 Threshold | Linear B Epitopes |
|---|---|---|---|
| SST (target antigen) (SEQ ID NO: 1) | 14 | 0 | 0% |
| Linker (SEQ ID NO: 10) | 19 | 16 | 84.2% |

TABLE 8-continued

B-cell epitope scores for Polypeptide Conjugate.

| Protein | # AA | # > 0.2 Threshold | Linear B Epitopes |
|---|---|---|---|
| CAT inactivated (carrier) (SEQ ID NO: 3) | 210 | 28 | 13.3% |
| Linker-SST (SEQ ID NO: 30) | 33 | 16 | 48.5% |
| CAT-linker-SST (SEQ ID NO: 13) | 243 | 45 | 18.5% |

A graph of the predicted B-cell epitope characteristics along the sequence of the polypeptide conjugate of SEQ ID NO: 13 is shown in FIG. 9. Remarkably, the linker having high % predicted linear B-cell epitopes imparts enhanced B-cell epitope characteristics to the polypeptide conjugate which results in improved immunogenicity of the target antigen, and improved immunological response/effect in the animal following administration, for example, as shown in improved rapid milk production, as shown in FIG. 4.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

What is claimed is:

1. A method for rapidly increasing milk production in an animal, the method comprising: administering an immunogenic amount of a vaccine to an animal, the vaccine comprising a polypeptide conjugate comprising a target antigen that is somatostatin-14 comprising the amino acid sequence of SEQ ID NO: 1, attached to an inactivated chloramphenicol acetyl transferase (CAT) enzyme by a linker polypeptide, wherein milk production is significantly increased within 4 days of the administration of the vaccine, relative to that of a control animal that does not receive administration of said vaccine.

2. The method according to claim 1, wherein the animal is a dairy cow, beef cow, goat, or sow.

3. The method according to claim 1, wherein peak milk production is achieved within 8-14 days of the administration of the vaccine.

4. The method according to claim 1, wherein the increase in milk production persists for at least 21 days.

5. The method according to claim 1, further comprising administering an additional immunogenic amount of the vaccine to the animal, wherein the additional administration is performed after peak milk production has been observed.

6. The method of claim 5, wherein the additional administration is performed after a return to baseline milk production has been observed.

7. The method of claim 6, wherein the additional administration is performed at intervals of approximately 21 days.

8. The method of claim 5, wherein subsequent administration of the vaccine does not produce an anamnestic response in the animal.

9. The method according to claim 1, wherein the inactivated CAT enzyme has one or more of 192 or 193 wild type histidine residues independently replaced with an amino acid selected from alanine, glycine, or other like amino acid.

10. The method according to claim 1, Wherein the inactivated CAT enzyme is truncated at the C-terminus by 10 amino acids relative to the wild type polypeptide.

11. The method according to claim 1, the inactivated CAT enzyme comprising the amino acid sequence selected from the group consisting of SEQ ID NOs: 3, 7, 8, 26, 27, 28 and 29.

12. The method according to claim 1, the linker polypeptide comprising the amino acid sequence repeat of $(Arg\text{-}Pro)_n$ or $(Lys\text{-}Pro)_n$, where n=2 to 6.

13. The method according to claim 1, the linker polypeptide comprising the amino acid sequence selected from the group consisting of SEQ ID NO: 10, 11, 16, 17, 18, 19, 20, 21, 22, 23, 24, 25, 53, 54, 55, 56 and 57.

14. The method according to claim 1, the polypeptide conjugate comprising the amino acid sequence of SEQ ID NO: 13.

15. The method according to claim 1, wherein the vaccine further comprises an adjuvant.

16. The method according to claim 15, wherein the adjuvant is an oil-in-water adjuvant.

17. The method according to claim 15, wherein the adjuvant comprises a carbopol and a squalene.

18. The method according to claim 17, wherein the adjuvant further comprises an arabinogalactan, or a tragacanth.

19. The method according to claim 1, wherein the immunogenic amount comprises a 1-2 mL dose of from 0.5-5 mg/mL of the polypeptide conjugate.

* * * * *

SEQUENCE LISTING

<160> NUMBER OF SEQ ID NOS: 57

<210> SEQ ID NO 1
<211> LENGTH: 14
<212> TYPE: PRT
<213> ORGANISM: Artificial Sequence
<220> FEATURE:
<223> OTHER INFORMATION: synthetic peptide- Somatostatin 14 target
      antigen

<400> SEQUENCE: 1

Ala Gly Cys Lys Asn Phe Phe Trp Lys Thr Phe Thr Ser Cys
1               5                   10

<210> SEQ ID NO 2
<211> LENGTH: 630
<212> TYPE: DNA
<213> ORGANISM: Artificial Sequence
<220> FEATURE:
<223> OTHER INFORMATION: Synthetic oligonucleotide encoding inactivated
      chloramphenicol acetyltransferase (CAT) polynucleotide encoding
      (His192->Gly, His193->Gly)

<400> SEQUENCE: 2

```
atggagaaaa aaatcactgg atataccacc gttgatatat cccaatggca tcgtaaagaa      60
cattttgagg catttcagtc agttgctcaa tgtacctata accagaccgt tcagctggat     120
attacggcct ttttaaagac cgtaaagaaa aataagcaca gtttttatcc ggcctttatt     180
cacattcttg cccgcctgat gaatgctcat ccggaattcc gtatggcaat gaaagacggt     240
gagctggtga tatgggatag tgttcaccct tgttacaccg ttttccatga gcaaactgaa     300
acgttttcat cgctctggag tgaataccac gacgatttcc ggcagtttct acacatatat     360
tcgcaagatg tggcgtgtta cggtgaaaac ctggcctatt tccctaaagg gtttattgag     420
```

```
aatatgtttt tcgtctcagc caatccctgg gtgagtttca ccagttttga tttaaacgtg    480
gccaatatgg acaacttctt cgcccccgtt ttcaccatgg gcaaatatta tacgcaaggc    540
gacaaggtgc tgatgccgct ggcgattcag gttggtggtg ccgtttgtga tggcttccat    600
gtcggccgta tgcttaatga actgcagcag                                    630
```

<210> SEQ ID NO 3
<211> LENGTH: 210
<212> TYPE: PRT
<213> ORGANISM: Artificial Sequence
<220> FEATURE:
<223> OTHER INFORMATION: Synthetic peptide-Model carrier polypeptide: inactivated CAT enzyme (corresponding to his-> gly at both 192 and 193)

<400> SEQUENCE: 3

```
Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
    50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Ala Pro Val Phe Thr Met Gly Lys Tyr Tyr
                165                 170                 175

Tyr Thr Gln Gly Asp Lys Val Leu Met Pro Leu Ala Ile Gln Val Gly
            180                 185                 190

Gly Ala Val Cys Asp Gly Phe His Val Gly Arg Met Leu Asn Glu Leu
        195                 200                 205

Gln Gln
    210
```

<210> SEQ ID NO 4
<211> LENGTH: 630
<212> TYPE: DNA
<213> ORGANISM: Artificial Sequence
<220> FEATURE:
<223> OTHER INFORMATION: Synthetic oligonucleotide encoding inactivated chloramphenicol acetyltransferase (CAT) polynucleotide encoding (His193->Gly)

<400> SEQUENCE: 4

```
atggagaaaa aaatcactgg atataccacc gttgatatat cccaatggca tcgtaaagaa    60
cattttgagg catttcagtc agttgctcaa tgtacctata accagaccgt tcagctggat   120
attacggcct ttttaaagac cgtaaagaaa aataagcaca gtttttatcc ggcctttatt   180
```

```
cacattcttg cccgcctgat gaatgctcat ccggaattcc gtatggcaat gaaagacggt    240
gagctggtga tatgggatag tgttcaccct tgttacaccg ttttccatga gcaaactgaa    300
acgttttcat cgctctggag tgaataccac gacgatttcc ggcagtttct acacatatat    360
tcgcaagatg tggcgtgtta cggtgaaaac ctggcctatt tccctaaagg gtttattgag    420
aatatgtttt tcgtctcagc caatccctgg gtgagtttca ccagttttga tttaaacgtg    480
gccaatatgg acaacttctt cgcccccgtt ttcaccatgg gcaaatatta tacgcaaggc    540
gacaaggtgc tgatgccgct ggcgattcag gttcatggtg ccgtttgtga tggcttccat    600
gtcggccgta tgcttaatga actgcagcag                                     630

<210> SEQ ID NO 5
<211> LENGTH: 630
<212> TYPE: DNA
<213> ORGANISM: Artificial Sequence
<220> FEATURE:
<223> OTHER INFORMATION: Synthetic oligonucleotide encoding inactivated
      chloramphenicol acetyltransferase (CAT) polynucleotide encoding
      (1 His193->Ala)

<400> SEQUENCE: 5
atggagaaaa aaatcactgg atataccacc gttgatatat cccaatggca tcgtaaagaa     60
cattttgagg catttcagtc agttgctcaa tgtacctata accagaccgt tcagctggat    120
attacggcct ttttaaagac cgtaaagaaa aataagcaca gtttatcc ggcctttatt      180 cacattcttg cccgcctgat gaatgctcat ccggaattcc gtatggcaat gaaagacggt    240
gagctggtga tatgggatag tgttcaccct tgttacaccg ttttccatga gcaaactgaa    300
acgttttcat cgctctggag tgaataccac gacgatttcc ggcagtttct acacatatat    360
tcgcaagatg tggcgtgtta cggtgaaaac ctggcctatt tccctaaagg gtttattgag    420
aatatgtttt tcgtctcagc caatccctgg gtgagtttca ccagttttga tttaaacgtg    480
gccaatatgg acaacttctt cgcccccgtt ttcaccatgg gcaaatatta tacgcaaggc    540
gacaaggtgc tgatgccgct ggcgattcag gttcatgctg ccgtttgtga tggcttccat    600
gtcggccgta tgcttaatga actgcagcag                                     630

<210> SEQ ID NO 6
<211> LENGTH: 630
<212> TYPE: DNA
<213> ORGANISM: Artificial Sequence
<220> FEATURE:
<223> OTHER INFORMATION: Synthetic oligonucleotide encoding
      chloramphenicol acetyltransferase (CAT) polynucleotide
      (1 His+CAT wt)

<400> SEQUENCE: 6
atggagaaaa aaatcactgg atataccacc gttgatatat cccaatggca tcgtaaagaa     60
cattttgagg catttcagtc agttgctcaa tgtacctata accagaccgt tcagctggat    120
attacggcct ttttaaagac cgtaaagaaa aataagcaca gtttatcc ggcctttatt      180 cacattcttg cccgcctgat gaatgctcat ccggaattcc gtatggcaat gaaagacggt    240
gagctggtga tatgggatag tgttcaccct tgttacaccg ttttccatga gcaaactgaa    300
acgttttcat cgctctggag tgaataccac gacgatttcc ggcagtttct acacatatat    360
tcgcaagatg tggcgtgtta cggtgaaaac ctggcctatt tccctaaagg gtttattgag    420
aatatgtttt tcgtctcagc caatccctgg gtgagtttca ccagttttga tttaaacgtg    480
```

```
gccaatatgg acaacttctt cgcccccgtt ttcaccatgg gcaaatatta tacgcaaggc    540
gacaaggtgc tgatgccgct ggcgattcag gttcatggtg ccgtttgtga tggcttccat    600
gtcggcagaa tgcttaatga actgcagcag                                     630
```

<210> SEQ ID NO 7
<211> LENGTH: 210
<212> TYPE: PRT
<213> ORGANISM: Artificial Sequence
<220> FEATURE:
<223> OTHER INFORMATION: Synthetic peptide-Model carrier polypeptide:
      inactivated CAT enzyme (one H->G)

<400> SEQUENCE: 7

```
Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
    50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

Gly Ala Val Cys Asp Gly Phe His Val Gly Arg Met Leu Asn Glu Leu
        195                 200                 205

Gln Gln
    210
```

<210> SEQ ID NO 8
<211> LENGTH: 210
<212> TYPE: PRT
<213> ORGANISM: Artificial Sequence
<220> FEATURE:
<223> OTHER INFORMATION: Synthetic peptide-Model carrier polypeptide:
      inactivated CAT enzyme with (H->A)

<400> SEQUENCE: 8

```
Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45
```

```
Lys Lys Asn Lys His Lys Phe Tyr Pro Ala Phe Ile His Ile Leu Ala
 50                  55                  60

Arg Leu Met Asn Ala His Pro Glu Phe Arg Met Ala Met Lys Asp Gly
 65                  70                  75                  80

Glu Leu Val Ile Trp Asp Ser Val His Pro Cys Tyr Thr Val Phe His
                 85                  90                  95

Glu Gln Thr Glu Thr Phe Ser Ser Leu Trp Ser Gly Tyr His Asp Asp
                100                 105                 110

Phe Arg Gln Phe Leu His Ile Tyr Ser Gln Asp Val Ala Cys Tyr Gly
                115                 120                 125

Glu Asn Leu Ala Tyr Phe Pro Lys Gly Phe Ile Glu Asn Met Phe Phe
130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
                180                 185                 190

Ala Ala Val Cys Asp Gly Phe His Val Gly Arg Met Leu Asn Glu Leu
                195                 200                 205

Gln Gln
    210

<210> SEQ ID NO 9
<211> LENGTH: 57
<212> TYPE: DNA
<213> ORGANISM: Artificial Sequence
<220> FEATURE:
<223> OTHER INFORMATION: Synthetic oligonucleotide encoding model linker

<400> SEQUENCE: 9
tgggaactgc accgttctgg tccacgcccg cgccctcgcc cacgtccgga attcatg          57

<210> SEQ ID NO 10
<211> LENGTH: 19
<212> TYPE: PRT
<213> ORGANISM: Artificial Sequence
<220> FEATURE:
<223> OTHER INFORMATION: synthetic linker polypeptide

<400> SEQUENCE: 10

Trp Glu Leu His Arg Ser Gly Pro Arg Pro Arg Pro Arg Pro Arg Pro
1               5                   10                  15

Glu Phe Met

<210> SEQ ID NO 11
<211> LENGTH: 15
<212> TYPE: PRT
<213> ORGANISM: Artificial Sequence
<220> FEATURE:
<223> OTHER INFORMATION: synthetic linker polypeptide

<400> SEQUENCE: 11

Trp Glu Leu His Arg Ser Gly Pro Arg Pro Arg Pro Glu Phe Met
1               5                   10                  15

<210> SEQ ID NO 12
<211> LENGTH: 729
<212> TYPE: DNA
<213> ORGANISM: Artificial Sequence
<220> FEATURE:
```

<223> OTHER INFORMATION: synthetic oligonucleotide encoding CAT-
      defective somatostatin fusion protein

<400> SEQUENCE: 12

```
atggagaaaa aaatcactgg atataccacc gttgatatat cccaatggca tcgtaaagaa        60
catttgagg catttcagtc agttgctcaa tgtacctata accagaccgt tcagctggat        120
attacggcct ttttaaagac cgtaaagaaa aataagcaca agttttatcc ggcctttatt       180
cacattcttg cccgcctgat gaatgctcat ccggaattcc gtatggcaat gaaagacggt       240
gagctggtga tatgggatag tgttcaccct tgttacaccg ttttccatga gcaaactgaa       300
acgttttcat cgctctggag tgaataccac gacgatttcc ggcagtttct acacatatat       360
tcgcaagatg tggcgtgtta cggtgaaaac ctggcctatt tccctaaagg gtttattgag       420
aatatgtttt tcgtctcagc caatccctgg gtgagtttca ccagttttga tttaaacgtg       480
gccaatatgg acaacttctt cgccccccgtt ttcaccatgg gcaaatatta tacgcaaggc       540
gacaaggtgc tgatgccgct ggcgattcag gttggtggtg ccgtttgtga tggcttccat       600
gtcggccgta tgcttaatga actgcagcag tgggaactgc accgttctgg tccacgcccg       660
cgccctcgcc cacgtccgga attcatggcc ggctgcaaga acttcttttg gaaaaccttt       720
acgagctgc                                                              729
```

<210> SEQ ID NO 13
<211> LENGTH: 243
<212> TYPE: PRT
<213> ORGANISM: Artificial Sequence
<220> FEATURE:
<223> OTHER INFORMATION: synthetic CAT-defective somatostatin fusion
      protein model polypeptide conjugate: carrier-linker-SST

<400> SEQUENCE: 13

```
Met Glu Lys Lys Ile Thr Gly Tyr Thr Thr Val Asp Ile Ser Gln Trp
  1               5                  10                  15

His Arg Lys Glu His Phe Glu Ala Phe Gln Ser Val Ala Gln Cys Thr
             20                  25                  30

Tyr Asn Gln Thr Val Gln Leu Asp Ile Thr Ala Phe Leu Lys Thr Val
         35                  40                  45

Lys Lys Asn Lys His Lys Phe Tyr Pro Ala Phe Ile His Ile Leu Ala
     50                  55                  60

Arg Leu Met Asn Ala His Pro Glu Phe Arg Met Ala Met Lys Asp Gly
 65                  70                  75                  80

Glu Leu Val Ile Trp Asp Ser Val His Pro Cys Tyr Thr Val Phe His
                 85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val Gly
            180                 185                 190

Gly Ala Val Cys Asp Gly Phe His Val Gly Arg Met Leu Asn Glu Leu
```

```
                195                 200                 205
Gln Gln Trp Glu Leu His Arg Ser Gly Pro Arg Pro Arg Pro
210                 215                 220

Arg Pro Glu Phe Met Ala Gly Cys Lys Asn Phe Phe Trp Lys Thr Phe
225                 230                 235                 240

Thr Ser Cys

<210> SEQ ID NO 14
<211> LENGTH: 243
<212> TYPE: PRT
<213> ORGANISM: Artificial Sequence
<220> FEATURE:
<223> OTHER INFORMATION: synthetic unmodified CAT-somatostatin fusion
      protein

<400> SEQUENCE: 14

Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
                20                  25                  30

Tyr Asn Gln Thr Val Gln Leu Asp Ile Thr Ala Phe Leu Lys Thr Val
            35                  40                  45

Lys Lys Asn Lys His Lys Phe Tyr Pro Ala Phe Ile His Ile Leu Ala
50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
                100                 105                 110

Phe Arg Gln Phe Leu His Ile Tyr Ser Gln Asp Val Ala Cys Tyr Gly
            115                 120                 125

Glu Asn Leu Ala Tyr Phe Pro Lys Gly Phe Ile Glu Asn Met Phe Phe
        130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln Trp Glu Leu His Arg Ser Gly Pro Arg Pro Arg Pro Arg Pro
210                 215                 220

Arg Pro Glu Phe Met Ala Gly Cys Lys Asn Phe Phe Trp Lys Thr Phe
225                 230                 235                 240

Thr Ser Cys

<210> SEQ ID NO 15
<211> LENGTH: 42
<212> TYPE: DNA
<213> ORGANISM: Artificial Sequence
<220> FEATURE:
<223> OTHER INFORMATION: Synthetic oligonucleotide; nucleic acid
      sequence encoding somatostatin-14

<400> SEQUENCE: 15
```

```
gctggctgca agaatttctt ctggaagact ttcacatcct gt                    42
```

<210> SEQ ID NO 16
<211> LENGTH: 17
<212> TYPE: PRT
<213> ORGANISM: Artificial Sequence
<220> FEATURE:
<223> OTHER INFORMATION: synthetic linker polypeptide

<400> SEQUENCE: 16

Trp Glu Leu His Arg Ser Gly Pro Arg Pro Arg Pro Arg Pro Glu Phe
1               5                   10                  15

Met

<210> SEQ ID NO 17
<211> LENGTH: 21
<212> TYPE: PRT
<213> ORGANISM: Artificial Sequence
<220> FEATURE:
<223> OTHER INFORMATION: synthetic linker polypeptide

<400> SEQUENCE: 17

Trp Glu Leu His Arg Ser Gly Pro Arg Pro Arg Pro Arg Pro Arg Pro
1               5                   10                  15

Arg Pro Glu Phe Met
            20

<210> SEQ ID NO 18
<211> LENGTH: 23
<212> TYPE: PRT
<213> ORGANISM: Artificial Sequence
<220> FEATURE:
<223> OTHER INFORMATION: synthetic linker polypeptide

<400> SEQUENCE: 18

Trp Glu Leu His Arg Ser Gly Pro Arg Pro Arg Pro Arg Pro Arg Pro
1               5                   10                  15

Arg Pro Arg Pro Glu Phe Met
            20

<210> SEQ ID NO 19
<211> LENGTH: 13
<212> TYPE: PRT
<213> ORGANISM: Artificial Sequence
<220> FEATURE:
<223> OTHER INFORMATION: synthetic linker polypeptide

<400> SEQUENCE: 19

Trp Glu Leu His Arg Ser Gly Pro Arg Pro Glu Phe Met
1               5                   10

<210> SEQ ID NO 20
<211> LENGTH: 19
<212> TYPE: PRT
<213> ORGANISM: Artificial Sequence
<220> FEATURE:
<223> OTHER INFORMATION: synthetic linker polypeptide

<400> SEQUENCE: 20

Trp Glu Leu His Arg Ser Gly Pro Lys Pro Lys Pro Lys Pro Lys Pro
1               5                   10                  15

Glu Phe Met

<210> SEQ ID NO 21

```
<211> LENGTH: 17
<212> TYPE: PRT
<213> ORGANISM: Artificial Sequence
<220> FEATURE:
<223> OTHER INFORMATION: synthetic linker polypeptide

<400> SEQUENCE: 21

Trp Glu Leu His Arg Ser Gly Pro Lys Pro Lys Pro Lys Pro Glu Phe
1               5                   10                  15

Met

<210> SEQ ID NO 22
<211> LENGTH: 15
<212> TYPE: PRT
<213> ORGANISM: Artificial Sequence
<220> FEATURE:
<223> OTHER INFORMATION: synthetic linker polypeptide

<400> SEQUENCE: 22

Trp Glu Leu His Arg Ser Gly Pro Lys Pro Lys Pro Glu Phe Met
1               5                   10                  15

<210> SEQ ID NO 23
<211> LENGTH: 13
<212> TYPE: PRT
<213> ORGANISM: Artificial Sequence
<220> FEATURE:
<223> OTHER INFORMATION: synthetic linker polypeptide

<400> SEQUENCE: 23

Trp Glu Leu His Arg Ser Gly Pro Lys Pro Glu Phe Met
1               5                   10

<210> SEQ ID NO 24
<211> LENGTH: 21
<212> TYPE: PRT
<213> ORGANISM: Artificial Sequence
<220> FEATURE:
<223> OTHER INFORMATION: synthetic linker polypeptide

<400> SEQUENCE: 24

Trp Glu Leu His Arg Ser Gly Pro Lys Pro Lys Pro Lys Pro Lys Pro
1               5                   10                  15

Lys Pro Glu Phe Met
            20

<210> SEQ ID NO 25
<211> LENGTH: 23
<212> TYPE: PRT
<213> ORGANISM: Artificial Sequence
<220> FEATURE:
<223> OTHER INFORMATION: synthetic linker polypeptide

<400> SEQUENCE: 25

Trp Glu Leu His Arg Ser Gly Pro Lys Pro Lys Pro Lys Pro Lys Pro
1               5                   10                  15

Lys Pro Lys Pro Glu Phe Met
            20

<210> SEQ ID NO 26
<211> LENGTH: 210
<212> TYPE: PRT
<213> ORGANISM: Artificial Sequence
<220> FEATURE:
<223> OTHER INFORMATION: Synthetic peptide-Model carrier polypeptide:
      inactivated CAT enzyme corresponding to (His192->Ala, His193->Ala)
```

<400> SEQUENCE: 26

Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
130                 135                 140

Val Ser Ala Asn Pro Trp Val Ser Phe Thr Ser Phe Asp Leu Asn Val
145                 150                 155                 160

Ala Asn Met Asp Asn Phe Ala Pro Val Phe Thr Met Gly Lys Tyr
                165                 170                 175

Tyr Thr Gln Gly Asp Lys Val Leu Met Pro Leu Ala Ile Gln Val Ala
            180                 185                 190

Ala Ala Val Cys Asp Gly Phe His Val Gly Arg Met Leu Asn Glu Leu
        195                 200                 205

Gln Gln
210

<210> SEQ ID NO 27
<211> LENGTH: 210
<212> TYPE: PRT
<213> ORGANISM: Artificial Sequence
<220> FEATURE:
<223> OTHER INFORMATION: Synthetic peptide-Model carrier polypeptide:
      inactivated CAT enzyme corresponding to (His192->Ala, His193->Gly)

<400> SEQUENCE: 27

Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
            130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val Ala
            180                 185                 190

Gly Ala Val Cys Asp Gly Phe His Val Gly Arg Met Leu Asn Glu Leu
        195                 200                 205

Gln Gln
    210

<210> SEQ ID NO 28
<211> LENGTH: 210
<212> TYPE: PRT
<213> ORGANISM: Artificial Sequence
<220> FEATURE:
<223> OTHER INFORMATION: Synthetic peptide-Model carrier polypeptide:
      inactivated CAT enzyme corresponding to (His192->Gly, His193->Ala)

<400> SEQUENCE: 28

Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
            85                  90                  95

Glu Gln Thr Glu Thr Phe Ser Ser Leu Trp Ser Glu Tyr His Asp Asp
        100                 105                 110

Phe Arg Gln Phe Leu His Ile Tyr Ser Gln Asp Val Ala Cys Tyr Gly
    115                 120                 125

Glu Asn Leu Ala Tyr Phe Pro Lys Gly Phe Ile Glu Asn Met Phe Phe
            130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val Gly
            180                 185                 190

Ala Ala Val Cys Asp Gly Phe His Val Gly Arg Met Leu Asn Glu Leu
        195                 200                 205

Gln Gln
    210

<210> SEQ ID NO 29
<211> LENGTH: 210
<212> TYPE: PRT
<213> ORGANISM: Artificial Sequence
<220> FEATURE:
<223> OTHER INFORMATION: Synthetic peptide-Model carrier polypeptide:

CAT enzyme with (His192, His193)

<400> SEQUENCE: 29

Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
    50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln
    210

<210> SEQ ID NO 30
<211> LENGTH: 33
<212> TYPE: PRT
<213> ORGANISM: Artificial Sequence
<220> FEATURE:
<223> OTHER INFORMATION: synthetic peptide-linker-SST fusion

<400> SEQUENCE: 30

Trp Glu Leu His Arg Ser Gly Pro Arg Pro Arg Pro Arg Pro Arg Pro
1               5                   10                  15

Glu Phe Met Ala Gly Cys Lys Asn Phe Phe Trp Lys Thr Phe Thr Ser
            20                  25                  30

Cys

<210> SEQ ID NO 31
<211> LENGTH: 326
<212> TYPE: PRT
<213> ORGANISM: Mycobacterium tuberculosis
<220> FEATURE:
<221> NAME/KEY: PEPTIDE
<222> LOCATION: (1)..(326)
<223> OTHER INFORMATION: amino acid sequence of M. tuberculosis H37Rv
      (GB:AL123456): Rv0899 - outer membrane protein A (OmpA Tb) target
      antigen

<400> SEQUENCE: 31

Met Ala Ser Lys Ala Gly Leu Gly Gln Thr Pro Ala Thr Thr Asp Ala

-continued

```
1               5                   10                  15

Arg Arg Thr Gln Lys Phe Tyr Arg Gly Ser Pro Gly Arg Pro Trp Leu
            20                  25                  30

Ile Gly Ala Val Val Ile Pro Leu Leu Ile Ala Ala Ile Gly Tyr Gly
        35                  40                  45

Ala Phe Glu Arg Pro Gln Ser Val Thr Gly Pro Thr Gly Val Leu Pro
    50                  55                  60

Thr Leu Thr Pro Thr Ser Thr Arg Gly Ala Ser Ala Leu Ser Leu Ser
65                  70                  75                  80

Leu Leu Ser Ile Ser Arg Ser Gly Asn Thr Val Thr Leu Ile Gly Asp
                85                  90                  95

Phe Pro Asp Glu Ala Ala Lys Ala Ala Leu Met Thr Ala Leu Asn Gly
            100                 105                 110

Leu Leu Ala Pro Gly Val Asn Val Ile Asp Gln Ile His Val Asp Pro
        115                 120                 125

Val Val Arg Ser Leu Asp Phe Ser Ser Ala Glu Pro Val Phe Thr Ala
    130                 135                 140

Ser Val Pro Ile Pro Asp Phe Gly Leu Lys Val Glu Arg Asp Thr Val
145                 150                 155                 160

Thr Leu Thr Gly Thr Ala Pro Ser Ser Glu His Lys Asp Ala Val Lys
                165                 170                 175

Arg Ala Ala Thr Ser Thr Trp Pro Asp Met Lys Ile Val Asn Asn Ile
            180                 185                 190

Glu Val Thr Gly Gln Ala Pro Pro Gly Pro Pro Ala Ser Gly Pro Cys
        195                 200                 205

Ala Asp Leu Gln Ser Ala Ile Asn Ala Val Thr Gly Gly Pro Ile Ala
    210                 215                 220

Phe Gly Asn Asp Gly Ala Ser Leu Ile Pro Ala Asp Tyr Glu Ile Leu
225                 230                 235                 240

Asn Arg Val Ala Asp Lys Leu Lys Ala Cys Pro Asp Ala Arg Val Thr
                245                 250                 255

Ile Asn Gly Tyr Thr Asp Asn Thr Gly Ser Glu Gly Ile Asn Ile Pro
            260                 265                 270

Leu Ser Ala Gln Arg Ala Lys Ile Val Ala Asp Tyr Leu Val Ala Arg
        275                 280                 285

Gly Val Ala Gly Asp His Ile Ala Thr Val Gly Leu Gly Ser Val Asn
    290                 295                 300

Pro Ile Ala Ser Asn Ala Thr Pro Glu Gly Arg Ala Lys Asn Arg Arg
305                 310                 315                 320

Val Glu Ile Val Val Asn
                325
```

<210> SEQ ID NO 32
<211> LENGTH: 17
<212> TYPE: PRT
<213> ORGANISM: Artificial Sequence
<220> FEATURE:
<223> OTHER INFORMATION: Synthetic peptide-OmpATb 32-48 target antigen fragment

<400> SEQUENCE: 32

```
Leu Ile Gly Ala Val Val Ile Pro Leu Leu Ile Ala Ala Ile Gly Tyr
1               5                   10                  15

Gly
```

```
<210> SEQ ID NO 33
<211> LENGTH: 12
<212> TYPE: PRT
<213> ORGANISM: Artificial Sequence
<220> FEATURE:
<223> OTHER INFORMATION: Synthetic peptide- OmpATb 75-86 target antigen
      fragment

<400> SEQUENCE: 33

Ser Ala Leu Ser Leu Ser Leu Leu Ser Ile Ser Arg
1               5                   10

<210> SEQ ID NO 34
<211> LENGTH: 31
<212> TYPE: PRT
<213> ORGANISM: Artificial Sequence
<220> FEATURE:
<223> OTHER INFORMATION: Synthetic peptide- OmpATb 104-134 target
      antigen fragment

<400> SEQUENCE: 34

Ala Ala Leu Met Thr Ala Leu Asn Gly Leu Leu Ala Pro Gly Val Asn
1               5                   10                  15

Val Ile Asp Gln Ile His Val Asp Pro Val Val Arg Ser Leu Asp
            20                  25                  30

<210> SEQ ID NO 35
<211> LENGTH: 11
<212> TYPE: PRT
<213> ORGANISM: Artificial Sequence
<220> FEATURE:
<223> OTHER INFORMATION: Synthetic peptide- OmpATb 235-246 target
      antigen fragment

<400> SEQUENCE: 35

Ala Asp Tyr Glu Ile Leu Asn Arg Val Ala Asp
1               5                   10

<210> SEQ ID NO 36
<211> LENGTH: 18
<212> TYPE: PRT
<213> ORGANISM: Artificial Sequence
<220> FEATURE:
<223> OTHER INFORMATION: Synthetic peptide- OmpATb 271-289 target
      antigen fragment

<400> SEQUENCE: 36

Pro Leu Ser Ala Gln Arg Ala Lys Ile Val Ala Asp Tyr Leu Val Ala
1               5                   10                  15

Arg Gly

<210> SEQ ID NO 37
<211> LENGTH: 10
<212> TYPE: PRT
<213> ORGANISM: Artificial Sequence
<220> FEATURE:
<223> OTHER INFORMATION: Synthetic peptide- OmpATb294-302 target
      antigen fragment

<400> SEQUENCE: 37

His Ile Ala Thr Val Gly Leu Gly Ser Val
1               5                   10

<210> SEQ ID NO 38
<211> LENGTH: 8
<212> TYPE: PRT
<213> ORGANISM: Artificial Sequence
```

```
<220> FEATURE:
<223> OTHER INFORMATION: Synthetic peptide- OmpATb 319-326 target
      antigen fragment

<400> SEQUENCE: 38

Arg Arg Val Glu Ile Val Val Asn
1               5

<210> SEQ ID NO 39
<211> LENGTH: 10
<212> TYPE: PRT
<213> ORGANISM: Artificial Sequence
<220> FEATURE:
<223> OTHER INFORMATION: Synthetic peptide- GnRH 1-10 target antigen
<220> FEATURE:
<221> NAME/KEY: MISC_FEATURE
<222> LOCATION: (1)..(1)
<223> OTHER INFORMATION: PYRROLIDINE CARBOXYLIC ACID
<220> FEATURE:
<221> NAME/KEY: MISC_FEATURE
<222> LOCATION: (10)..(10)
<223> OTHER INFORMATION: AMIDATION

<400> SEQUENCE: 39

Glu His Trp Ser Tyr Gly Leu Arg Pro Gly
1               5                   10

<210> SEQ ID NO 40
<211> LENGTH: 8
<212> TYPE: PRT
<213> ORGANISM: Artificial Sequence
<220> FEATURE:
<223> OTHER INFORMATION: Synthetic peptide- GnRH1 1-8 target antigen
      fragment

<400> SEQUENCE: 40

Glu His Trp Ser Tyr Gly Leu Arg
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic peptide- GnRH1 1-9 target antigen
      fragment

<400> SEQUENCE: 41

Glu His Trp Ser Tyr Gly Leu Arg Pro
1               5

<210> SEQ ID NO 42
<211> LENGTH: 139
<212> TYPE: PRT
<213> ORGANISM: Homo sapiens
<220> FEATURE:
<221> NAME/KEY: PEPTIDE
<222> LOCATION: (1)..(139)
<223> OTHER INFORMATION: calcitonin neuropeptide-preprocalcitonin target
      antigen

<400> SEQUENCE: 42

Met Gly Phe Gln Lys Phe Ser Pro Phe Leu Ala Leu Ser Ile Leu Val
1               5                   10                  15

Leu Leu Gln Ala Gly Ser Leu His Ala Ala Pro Phe Arg Ser Ala Leu
            20                  25                  30

Glu Ser Ser Pro Ala Pro Ala Thr Leu Ser Glu Asp Glu Ala Arg Leu
        35                  40                  45
```

```
Leu Leu Ala Ala Leu Val Gln Asn Tyr Val Gln Met Lys Ala Ser Glu
 50                  55                  60

Leu Glu Gln Glu Gln Glu Arg Glu Gly Ser Ser Leu Asp Ser Pro Arg
 65                  70                  75                  80

Ser Lys Arg Cys Gly Asn Leu Ser Thr Cys Met Leu Gly Thr Tyr Thr
                 85                  90                  95

Gln Asp Phe Asn Lys Phe His Thr Phe Pro Gln Thr Ala Ile Gly Val
            100                 105                 110

Gly Ala Pro Gly Lys Lys Arg Asp Met Ser Ser Asp Leu Glu Arg Asp
        115                 120                 125

His Arg Pro His Val Ser Met Pro Gln Asn Ala
    130                 135
```

```
<210> SEQ ID NO 43
<211> LENGTH: 21
<212> TYPE: PRT
<213> ORGANISM: Artificial Sequence
<220> FEATURE:
<223> OTHER INFORMATION: Synthetic peptide- Calcitonin 85-105 AA target
      antigen fragment

<400> SEQUENCE: 43

Cys Gly Asn Leu Ser Thr Cys Met Leu Gly Thr Tyr Thr Gln Asp Phe
1               5                   10                  15

Asn Lys Phe His Thr
            20
```

```
<210> SEQ ID NO 44
<211> LENGTH: 36
<212> TYPE: PRT
<213> ORGANISM: Artificial Sequence
<220> FEATURE:
<223> OTHER INFORMATION: Synthetic peptide- Calcitonin AA 81-116 target
      antigen fragment

<400> SEQUENCE: 44

Arg Ser Lys Arg Cys Gly Asn Leu Ser Thr Cys Met Leu Gly Thr Tyr
1               5                   10                  15

Thr Gln Asp Phe Asn Lys Phe His Thr Phe Pro Gln Thr Ala Ile Gly
            20                  25                  30

Val Gly Ala Pro
        35
```

```
<210> SEQ ID NO 45
<211> LENGTH: 375
<212> TYPE: PRT
<213> ORGANISM: Homo sapiens
<220> FEATURE:
<221> NAME/KEY: PEPTIDE
<222> LOCATION: (1)..(375)
<223> OTHER INFORMATION: myostatin target antigen

<400> SEQUENCE: 45

Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60
```

Arg Leu Glu Thr Ala Pro Asn Ile Ser Lys Asp Val Ile Arg Gln Leu
 65                  70                  75                  80

Leu Pro Lys Ala Pro Pro Leu Arg Glu Leu Ile Asp Gln Tyr Asp Val
                 85                  90                  95

Gln Arg Asp Asp Ser Ser Asp Gly Ser Leu Glu Asp Asp Tyr His
            100                 105                 110

Ala Thr Thr Glu Thr Ile Ile Thr Met Pro Thr Glu Ser Asp Phe Leu
            115                 120                 125

Met Gln Val Asp Gly Lys Pro Lys Cys Cys Phe Phe Lys Phe Ser Ser
130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
            195                 200                 205

Lys Thr Val Leu Gln Asn Trp Leu Lys Gln Pro Glu Ser Asn Leu Gly
210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
            275                 280                 285

Asp Phe Glu Ala Phe Gly Trp Asp Trp Ile Ile Ala Pro Lys Arg Tyr
290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
            355                 360                 365

Val Asp Arg Cys Gly Cys Ser
            370                 375

<210> SEQ ID NO 46
<211> LENGTH: 20
<212> TYPE: PRT
<213> ORGANISM: Artificial Sequence
<220> FEATURE:
<223> OTHER INFORMATION: Synthetic peptide- Myostatin1-20 target antigen
      fragment

<400> SEQUENCE: 46

Met Gln Lys Leu Gln Leu Cys Val Tyr Ile Tyr Leu Phe Met Leu Ile
 1               5                  10                  15

Val Ala Gly Pro
            20

```
<210> SEQ ID NO 47
<211> LENGTH: 17
<212> TYPE: PRT
<213> ORGANISM: Artificial Sequence
<220> FEATURE:
<223> OTHER INFORMATION: Synthetic peptide- Myostatin 52-68 target
      antigen fragment

<400> SEQUENCE: 47

Arg Ile Glu Ala Ile Lys Ile Gln Ile Leu Ser Lys Leu Arg Leu Glu
1               5                   10                  15

Thr

<210> SEQ ID NO 48
<211> LENGTH: 28
<212> TYPE: PRT
<213> ORGANISM: Artificial Sequence
<220> FEATURE:
<223> OTHER INFORMATION: Synthetic peptide- Myostatin136-162 target
      antigen fragment

<400> SEQUENCE: 48

Lys Cys Cys Phe Phe Lys Phe Ser Ser Lys Ile Gln Tyr Asn Lys Val
1               5                   10                  15

Val Lys Ala Gln Leu Trp Ile Tyr Leu Arg Pro Val
            20                  25

<210> SEQ ID NO 49
<211> LENGTH: 13
<212> TYPE: PRT
<213> ORGANISM: Artificial Sequence
<220> FEATURE:
<223> OTHER INFORMATION: Synthetic peptide- Myostatin 169-179 target
      antigen fragment

<400> SEQUENCE: 49

Thr Val Phe Val Gln Ile Leu Arg Leu Ile Lys Pro Met
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Synthetic peptide- Myostatin 204-216 target
      antigen fragment

<400> SEQUENCE: 50

Gln Ser Ile Asp Val Lys Thr Val Leu Gln Asn Trp Leu
1               5                   10

<210> SEQ ID NO 51
<211> LENGTH: 23
<212> TYPE: PRT
<213> ORGANISM: Artificial Sequence
<220> FEATURE:
<223> OTHER INFORMATION: Synthetic peptide- Myostatin 280-302 target
      antigen fragment

<400> SEQUENCE: 51

Arg Cys Cys Arg Tyr Pro Leu Thr Val Asp Phe Glu Ala Phe Gly Trp
1               5                   10                  15

Asp Trp Ile Ile Ala Pro Lys
            20

<210> SEQ ID NO 52
```

<210> SEQ ID NO 52
<211> LENGTH: 19
<212> TYPE: PRT
<213> ORGANISM: Artificial Sequence
<220> FEATURE:
<223> OTHER INFORMATION: Synthetic peptide- Myostatin 311-329 target
      antigen fragment

<400> SEQUENCE: 52

Gly Glu Cys Glu Phe Val Phe Leu Gln Lys Tyr Pro His Thr His Leu
1               5                   10                  15

Val His Gln

<210> SEQ ID NO 53
<211> LENGTH: 15
<212> TYPE: PRT
<213> ORGANISM: Artificial Sequence
<220> FEATURE:
<223> OTHER INFORMATION: Synthetic peptide- Linker Polypeptide Sequence

<400> SEQUENCE: 53

Pro Pro Lys Asp Thr Asn Gln Thr Gln Pro Ala Thr Gln Pro Ala
1               5                   10                  15

<210> SEQ ID NO 54
<211> LENGTH: 18
<212> TYPE: PRT
<213> ORGANISM: Artificial Sequence
<220> FEATURE:
<223> OTHER INFORMATION: Synthetic peptide- Plasmodium yoelii
      circumsporozoite (CS) protein B cell epitope (PyCS-B epitope3)
      Linker Polypeptide Sequence

<400> SEQUENCE: 54

Gln Gly Pro Gly Ala Pro Gln Gly Pro Gly Ala Pro Gln Gly Pro Gly
1               5                   10                  15

Ala Pro

<210> SEQ ID NO 55
<211> LENGTH: 12
<212> TYPE: PRT
<213> ORGANISM: Artificial Sequence
<220> FEATURE:
<223> OTHER INFORMATION: Synthetic peptide- PyCS-B epitope2 Linker
      Polypeptide Sequence

<400> SEQUENCE: 55

Gln Gly Pro Gly Ala Pro Gln Gly Pro Gly Ala Pro
1               5                   10

<210> SEQ ID NO 56
<211> LENGTH: 15
<212> TYPE: PRT
<213> ORGANISM: Artificial Sequence
<220> FEATURE:
<223> OTHER INFORMATION: Synthetic peptide- PyCS-B epitope4 Linker
      Polypeptide Sequence

<400> SEQUENCE: 56

Gln Gly Pro Gly Ala Pro Gln Gly Pro Gly Ala Pro Gln Gly Pro
1               5                   10                  15

<210> SEQ ID NO 57
<211> LENGTH: 8
<212> TYPE: PRT
<213> ORGANISM: Artificial Sequence
<220> FEATURE:
<223> OTHER INFORMATION: Synthetic peptide- Dengue Virus Type 1 B cell -continued

```
      epitope Linker Polypeptide Sequence

<400> SEQUENCE: 57

Glu His Lys Tyr Ser Trp Lys Ser
1               5
```